United States Patent
Mirowski et al.

(10) Patent No.: US 9,443,141 B2
(45) Date of Patent: Sep. 13, 2016

(54) METHOD, SYSTEM, AND COMPUTER-ACCESSIBLE MEDIUM FOR CLASSIFICATION OF AT LEAST ONE ICTAL STATE

(75) Inventors: Piotr W. Mirowski, New York, NY (US); Deepak Madhavan, Omaha, NE (US); Yann Lecun, Lincroft, NJ (US); Ruben Kuzniecky, Englewood, NJ (US)

(73) Assignee: New York University, New York, NY (US)

( * ) Notice: Subject to any disclaimer, the term of this patent is extended or adjusted under 35 U.S.C. 154(b) by 465 days.

(21) Appl. No.: 12/995,925

(22) PCT Filed: Jun. 2, 2009

(86) PCT No.: PCT/US2009/046028
§ 371 (c)(1),
(2), (4) Date: May 16, 2011

(87) PCT Pub. No.: WO2009/149126
PCT Pub. Date: Dec. 10, 2009

(65) Prior Publication Data
US 2011/0218950 A1    Sep. 8, 2011

Related U.S. Application Data

(60) Provisional application No. 61/058,107, filed on Jun. 2, 2008.

(51) Int. Cl.
*G06N 5/02* (2006.01)
*G06F 15/18* (2006.01)
(Continued)

(52) U.S. Cl.
CPC ......... *G06K 9/00536* (2013.01); *A61B 5/0476* (2013.01); *A61B 5/4094* (2013.01); *A61B 5/7267* (2013.01); *A61B 5/0402* (2013.01);
(Continued)

(58) Field of Classification Search
None
See application file for complete search history.

(56) References Cited

U.S. PATENT DOCUMENTS

| | | | | |
|---|---|---|---|---|
| 5,105,468 A | * | 4/1992 | Guyon | G06K 9/00416 382/158 |
| 5,725,472 A | * | 3/1998 | Weathers | A61M 21/0094 128/905 |

(Continued)

FOREIGN PATENT DOCUMENTS

| | | | |
|---|---|---|---|
| KR | WO-02081770 | 10/2002 | |
| KR | WO-2005085778 | 8/2005 | |
| WO | WO 9840824 A1 * | 9/1998 | ........... G06F 17/509 |

OTHER PUBLICATIONS

Christopher J. James, "Detection of epileptiform activity in the electroencephalogram using artificial neural networks," Ph.D. Thesis, University of Canterbury, Christchurch, New Zealand, Feb. 1997.*

(Continued)

*Primary Examiner* — Kakali Chaki
*Assistant Examiner* — Fuming Wu
(74) *Attorney, Agent, or Firm* — Andrews Kurth LLP

(57) ABSTRACT

An exemplary methodology, procedure, system, method and computer-accessible medium can be provided for receiving physiological data for the subject, extracting one or more patterns of features from the physiological data, and classifying the at least one state of the subject using a spatial structure and a temporal structure of the one or more patterns of features, wherein at least one of the at least one state is an ictal state.

49 Claims, 12 Drawing Sheets

(51) Int. Cl.
*G06K 9/00* (2006.01)
*A61B 5/0476* (2006.01)
*A61B 5/00* (2006.01)
*G06N 3/02* (2006.01)
*A61B 5/04* (2006.01)
*A61B 5/0402* (2006.01)

(52) U.S. Cl.
CPC ............ *A61B5/04008* (2013.01); *A61B 5/726* (2013.01); *A61B 5/7275* (2013.01); *G06N 3/02* (2013.01)

(56) References Cited

U.S. PATENT DOCUMENTS

| | | | | |
|---|---|---|---|---|
| 5,812,698 | A * | 9/1998 | Platt | G06K 9/00879 382/186 |
| 6,128,606 | A * | 10/2000 | Bengio | G06F 17/509 706/10 |
| 6,219,682 | B1 * | 4/2001 | Terashima | G06F 17/16 359/107 |
| 6,302,844 | B1 * | 10/2001 | Walker | A61B 5/1112 128/904 |
| 6,785,328 | B2 * | 8/2004 | Harikumar | H04L 25/03012 375/232 |
| 6,904,408 | B1 * | 6/2005 | McCarthy | A61B 5/6815 705/2 |
| 8,469,713 | B2 * | 6/2013 | Kron | G09B 23/28 434/156 |
| 2002/0103512 | A1 * | 8/2002 | Echauz | A61B 5/0482 607/9 |
| 2003/0002731 | A1 * | 1/2003 | Wersing | G06K 9/4628 382/161 |
| 2003/0158587 | A1 * | 8/2003 | Esteller | A61B 5/0482 607/45 |
| 2004/0260550 | A1 * | 12/2004 | Burges | G10L 17/00 704/259 |
| 2005/0113650 | A1 * | 5/2005 | Pacione | A61B 5/411 600/300 |
| 2005/0113703 | A1 * | 5/2005 | Farringdon | A61B 5/0428 600/509 |
| 2005/0288954 | A1 * | 12/2005 | McCarthy | A61B 5/6815 705/2 |
| 2006/0025697 | A1 * | 2/2006 | Kurzweil | A61B 5/0452 600/509 |
| 2006/0034495 | A1 * | 2/2006 | Miller | G06K 9/00214 382/118 |
| 2006/0056704 | A1 * | 3/2006 | Bachmann | G06K 9/6256 382/224 |
| 2006/0110040 | A1 * | 5/2006 | Simard | G06K 9/00422 382/181 |
| 2007/0149952 | A1 * | 6/2007 | Bland | G06F 19/345 604/890.1 |
| 2007/0150024 | A1 * | 6/2007 | Leyde | A61B 5/0476 607/45 |
| 2007/0150025 | A1 * | 6/2007 | Dilorenzo | A61B 5/0476 607/45 |
| 2007/0213786 | A1 * | 9/2007 | Sackellares | A61B 5/0476 607/45 |
| 2007/0287931 | A1 * | 12/2007 | Dilorenzo | A61B 5/0476 600/545 |
| 2008/0052259 | A1 * | 2/2008 | Shiffman | G06N 5/025 706/47 |
| 2008/0097175 | A1 * | 4/2008 | Boyce | A61B 5/0255 600/323 |
| 2008/0139898 | A1 * | 6/2008 | Johnson | A61B 5/0002 600/301 |
| 2008/0183096 | A1 * | 7/2008 | Snyder | G06K 9/00496 600/545 |
| 2008/0208781 | A1 * | 8/2008 | Snyder | G06F 19/34 706/20 |
| 2008/0234598 | A1 * | 9/2008 | Snyder | A61B 5/0006 600/545 |
| 2008/0235284 | A1 * | 9/2008 | Aarts | A61B 5/0533 |
| 2011/0218950 | A1 * | 9/2011 | Mirowski | A61B 5/0476 706/12 |
| 2011/0282169 | A1 * | 11/2011 | Grudic | G06F 19/3437 600/324 |

OTHER PUBLICATIONS

Klaus Lehnertz et al. "The First International Collaborative Workshop on Seizure Prediction: summary and data description," Elsevier Ireland, Available online Jan. 5, 2005.*

Perkins et al., "Grafting: Fast, Incremental Feature Selection by Gradient Descent in Function Space," Journal of Machine Learning Research 3 (2003) 1333-1356.*

Bengio et al., "Globally Trained Handwritten Word Recognizer using Special Representation Convolutional Neural Network and Hidden Markov Model," Globally Trained Handwritten Word Recognizer, pp. 937-944, 1994.*

Perkins et al., "Grafting: Fast, Incremental Feature Selection by Gradient Descent in Function Space," Journal of Machine Learning Research 3 (2003) 1333-1356, 2003.*

Bengio. et al., "Globally Trained Handwritten Word Recognizer using Special Representation Convolutional Neural Network and Hidden Markov Model," Globally Trained Handwritten Word Recognizer, pp. 937-944, 1994.*

Bengio. et al., "LeRec: A NN/HMM Hybrid for On Line Handwriting Recognition," Neural Computation, vol. 7, No. 6, pp. 1-5, 1995.*

LeCun. et al., "Convolutional Networks for Images, Speech, and Time-Series," The Handbook of Brain Theory and Neural Networks, MIT Press, M. Arbib (editor) : pp. 255-258, 1995.*

Mirowski. et al., "Classification of Patterns of EEG Synchronization for Seizure Prediction," The 2008 American Epilepsy Society annual meeting, and, The 2008 IEEE Workshop on Machine Learning for Signal Processing, 25 pp., 2008.*

Perkins. et al., "Grafting: Fast, Incremental Feature Selection by Gradient Descent in Function Space," Journal of Machine Learning Research 3 (2003), pp. 1333-1356, 2003.*

Zhou. et al., "On the Use of Hidden Markov Modeling and Time-frequency Features for Damage Classification in Composite Structures", Journal of Intelligent Material Systems and Structures, vol. 20, pp. 1271-1288, Jul. 2009.*

D'Alessandro, Maryann et al., "Epileptic Seizure Prediction using Hybrid Feature Selection over Multiple Intracranial EEG Electrode Contacts: A Report of Four Patients", *IEEE Transactions on Biomedical Engineering*, vol. 50, No. 5, May 2003, 603-615.

* cited by examiner

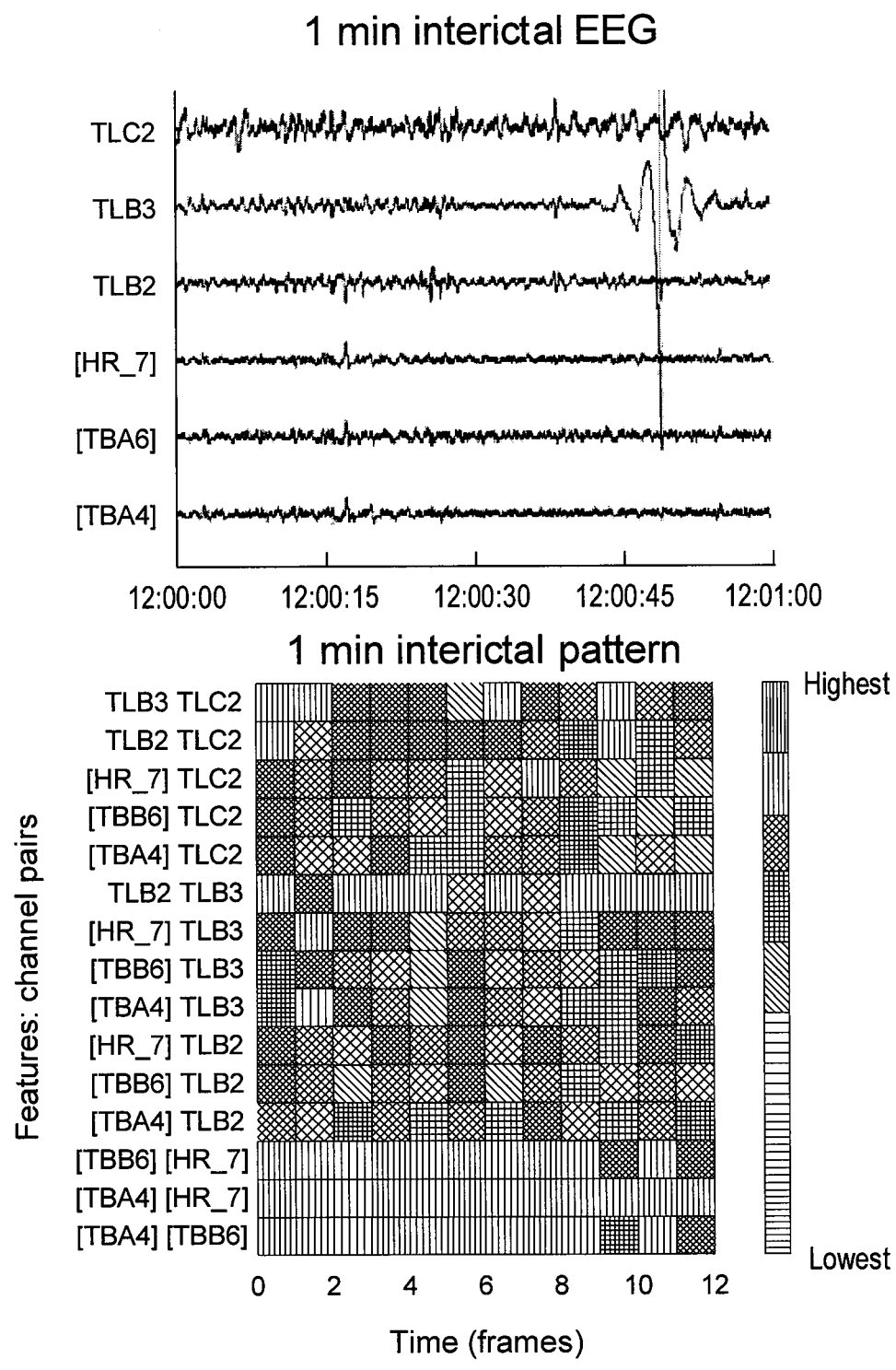
F I G. 1(a)

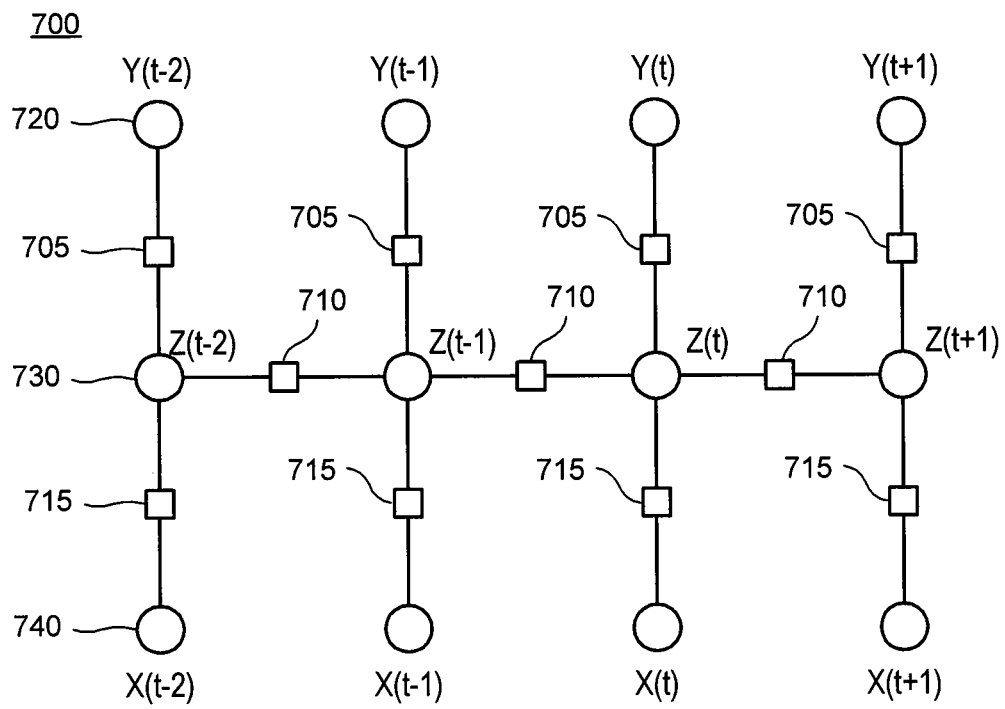
F I G. 7(a)
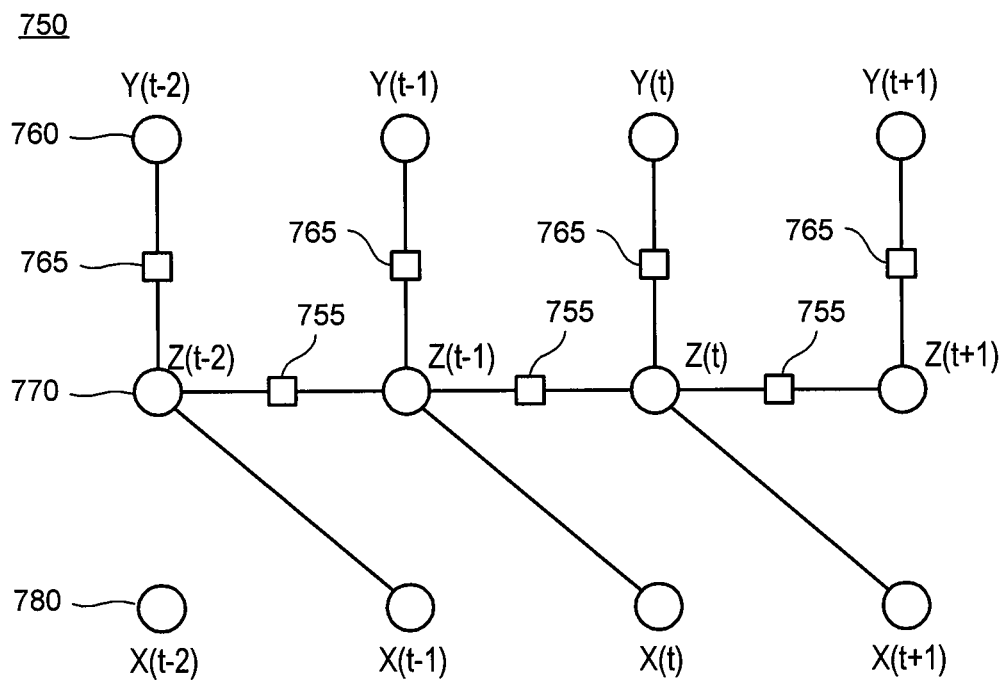
F I G. 7(b)

METHOD, SYSTEM, AND COMPUTER-ACCESSIBLE MEDIUM FOR CLASSIFICATION OF AT LEAST ONE ICTAL STATE

CROSS-REFERENCE TO RELATED APPLICATIONS

The present application is a U.S. National Phase of International Application PCT/US2009/046028 filed Jun. 2, 2009, and also relates to and claims priority from U.S. Patent Application Ser. No. 61/058,107 filed Jun. 2, 2008, the entire disclosures of which are hereby incorporated herein by reference in their entireties.

FIELD OF THE DISCLOSURE

The present disclosure relates to exemplary embodiments of system, method and computer-accessible medium for the classification of at least one ictal state.

BACKGROUND INFORMATION

Epilepsy is a disorder of the brain characterized by chronic, recurring seizures. Seizures can be a result of uncontrolled discharges of electrical activity in the brain. A seizure typically manifests as sudden, involuntary, disruptive, and often destructive sensory, motor, and cognitive phenomena.

One tool for evaluating the physiological states of the brain is the electroencephalogram (EEG). The standard for analysis and interpretation of the EEG is visual inspection of the graphic tracing of the EEG by a trained clinical electroencephalographer. It can be difficult to predict a seizure onset by visual analysis of the EEG. Traditional signal processing techniques yield little practical information about the EEG signal.

Recent multi-center clinical studies showed evidence of premonitory symptoms in 6.2% of 500 patients with epilepsy (See "Seizure anticipation by patients with focal and generalized epilepsy: a multicentre assessment of premonitory symptoms" by Schulze-Bonhage et al., 2006). Another interview-based study found that 50% of 562 patients felt "auras" before seizures (See "Hungarian multicentre epidemiologic study of the warning and initial symptoms of epileptic seizures" by Rajna et al., 1997). Such clinical observations give an incentive to search for premonitory changes on EEG recordings from the brain.

Current seizure prediction approaches can be summarized into, e.g., (1) extracting measurements from EEG over time, and (2) classifying them into a preictal or interictal state. The ictal and postictal states can be discarded from the classification, because the task is not to detect undergoing seizures, but eventually to warn the patient about future seizures, so that the patient, the clinician and/or an implanted device can act accordingly.

Certain techniques provide, with less than desirable accuracy, seizure detection during the very early stages of a seizure discharge in the EEG (e.g., a few seconds after the initial discharge). Techniques capable of providing true seizure prediction and/or warning would likely be of high importance, not only to those afflicted with seizure disorders, but also to those members of the medical community who are committed to providing care and effective treatment for those who suffer from epileptic seizure related conditions.

Thus, it can be desirable to provide a method and apparatus for predicting seizures with such accuracy that the activity of the brain can be monitored so that preventative actions through application of intervention measures to abort or modulate the seizure prior to clinical onset.

SUMMARY OF EXEMPLARY EMBODIMENTS OF DISCLOSURE

At least some of the above described problems can be addressed by exemplary embodiments of the system, method and computer accessible medium according to the present disclosure. For example, using such exemplary embodiments, it is possible to receive physiological data for the subject, extract one or more patterns of features from the physiological data, and using a computing arrangement, classify the at least one state of the subject using a spatial structure and a temporal structure of the one or more patterns of features, wherein at least one of the at least one state is an ictal state.

The computing arrangement can comprise a trained classifier executed by a computer. Each of the features can be a measurement between at least two channels for measuring the physiological data. Each of the channels can be provided at a different location on an anatomical structure from a location of another one of the channels. The anatomical structure can comprise a brain.

The one or more patterns of features can be represented by two-dimensional data, which can be data of time versus a pair of channels, or time versus a pair of channels and frequency. The one or more patterns of features can be represented by three-dimensional data, which can be data of time versus a pair of channels versus frequency.

The computing arrangement can classify the at least one ictal state of the subject using convolutional networks. The at least one ictal state can comprise at least one of an ictal classification, a peri-ictal classification, a pre-ictal classification or an interictal classification. The physiological data can be at least one of EEG data, multi-channel EEG data, fMRI data, MEG data, EKG data, pulse data, respiration data, temperature data, eye movement data or blood chemistry data. The one or more patterns of features can be spatially-varying and time-varying, and can be frequency-varying. The at least one state can comprise at least one of a seizure, a stroke or a headache. The classifying procedure can comprise discriminating between pre-ictal and inter-ictal states. The temporal structure of the one or more patterns of features can comprise a local time structure.

The features can comprise bivariate features, which can be based on a measure of a synchronization among one or more subsets of the physiological data. The measure of the synchronization can be based on at least one of a cross-correlation, a nonlinear interdependence, a difference of Lyapunov exponents or a phase-locking synchrony. The measure of the synchronization can be based on wavelet analysis-based synchrony values grouped in one or more frequency bands. The synchrony can comprise one of a phase-locking statistic, an entropy of a phase difference and distribution, or a coherence.

The classifying procedure can be performed using at least one of a logistic regression or a support vector machine. The features can be unaveraged. The classifying procedure can comprise regularizing the at least one state using a lasso regularization or an L1-norm regularization. The classifying procedure can comprise regularizing the at least one state using a ridge regularization or an L2-norm regularization. The classifying procedure can comprise training the at least one state using a stochastic gradient descent. The classifying procedure can also comprise training the at least one state by determining finite impulse response filters of at least a portion of the features. The features can be consecutive features.

The method can further comprise performing a sensitivity analysis on the patterns of features before classifying the at least one state. The sensitivity analysis can be used to evaluate an importance of a particular feature according to a spatial location, time or a frequency location in the pattern of features thereof.

The method can further comprise electronically storing the received physiological data, receiving further physiological data for the subject, extracting one or more further patterns of features from the further physiological data of the subject, and using the computing arrangement, classifying the at least one state of the subject based on the patterns of features from the received physiological data and the further patterns of features based on the further physiological data.

Using such exemplary embodiments, it is also possible to provide a computer-accessible medium for classifying at least one state of a subject, the computer-accessible medium including instructions thereon, wherein, when a computing arrangement executes the instructions, the computing arrangement is configured to perform procedures comprising receiving physiological data for the subject, extracting one or more patterns of features from the physiological data of the subject, and using a computing arrangement for classifying the at least one state of the subject using at least one of a spatial structure and a temporal structure of the one or more patterns of features, wherein at least one of the at least one state is an ictal state.

Using such exemplary embodiments, it is also possible to provide a system for classifying at least one state of a subject, comprising an input module, which, when executed by a computing arrangement, causes the computing arrangement to obtain one or more first extracted patterns of features from physiological data of a subject at a particular time interval, and a classifier module, which, when executed by the computing arrangement, causes the computing arrangement to classify at least one state of the subject using at least one of a spatial and temporal structure of the one or more extracted patterns of features, wherein at least one of the at least one state is an ictal state.

The system can further comprise an output module, which, when executed by the computing arrangement, causes the computing arrangement to output the at least one state of the subject at the particular time interval. The system can further comprise an electronic storage arrangement which stores the physiological data of the subject at the particular time interval and the at least one state of the subject.

The system can further comprise a further input module, which, when executed by the computing arrangement, causes the computing arrangement to obtain one or more further extracted patterns of features from the physiological data of the subject at a further time interval, and a further classifier module, which, when executed by the computing arrangement, causes the computing arrangement to classify at least one further ictal state of the subject using at least one of a spatial structure and a temporal structure of the one or more further extracted patterns of features, and the at least one state stored in the electronic storage arrangement.

The classifier can comprise a support vector machine and the patterns of features that are in a training dataset and that serve as support vectors for the classifier can be used to evaluate an electrophysiological recording or the development of ictal states over time.

These and other objects, features and advantages of the present disclosure will become apparent upon reading the following detailed description of embodiments of the present disclosure, when taken in conjunction with the appended claims.

BRIEF DESCRIPTION OF THE DRAWINGS

The foregoing and other exemplary objects of the present disclosure will be apparent upon consideration of the following detailed description, taken in conjunction with the accompanying exemplary drawings and claims, in which like reference characters refer to like parts throughout, and in which:

FIG. 1a is an illustration of an exemplary graph of a 1-minute EEG recording and its corresponding pattern of cross-correlation features for interictal recordings for a particular patient;

FIG. 1b is an illustration of an exemplary graph of a 1-minute EEG recording and corresponding pattern of cross-correlation features for preictal recordings for the same patient as in FIG. 1a;

FIGS. 7a and 7b illustrate exemplary graphs of state space models using temporal dynamics that can be used for seizure prediction systems;

Figure 1B:
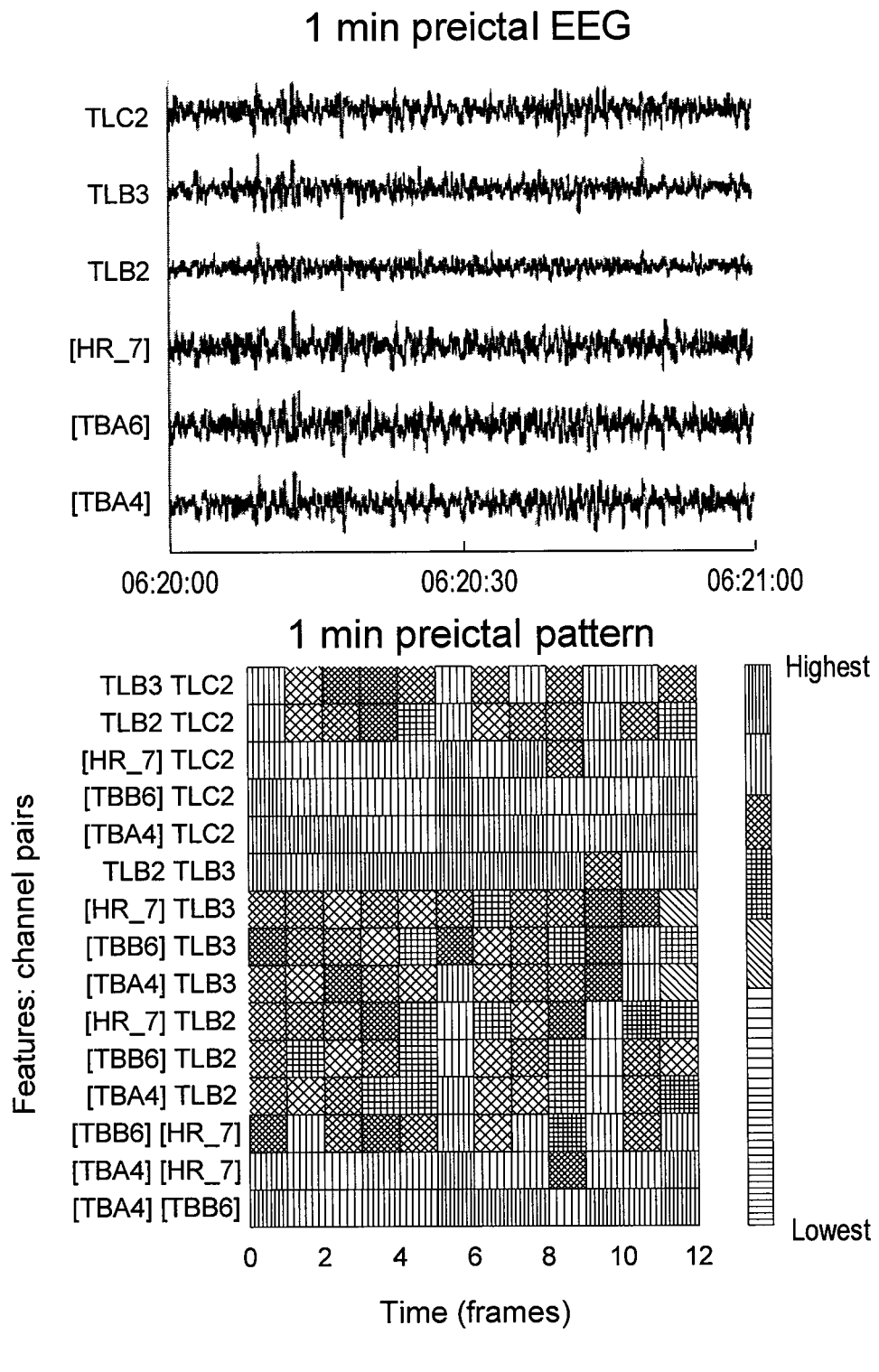

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention.

DETAILED DESCRIPTION OF EXEMPLARY EMBODIMENTS OF THE DISCLOSURE

Exemplary embodiments of the methodology and procedure which can be implemented by the exemplary system, method and computer-accessible medium according to the present disclosure will now be described with reference to the figures.

Exemplary Feature Extraction from EEG

Seizure prediction methods can have in common an initial building block comprising the extraction of EEG features. All EEG features can be computed over a short time window of a few seconds to a few minutes. Univariate measures, which can be computed or determined, e.g., using a computer arrangement on each EEG channel separately, and bivariate (or multivariate) measures, which can quantify some relationship, such as synchronization, can be distinguished between two or more EEG channels.

Described herein are four exemplary types of EEG synchronization (bivariate) features: an exemplary linear feature Maximum Cross-Correlation, and three nonlinear features.

In an exemplary embodiment of the present disclosure which uses a Maximum Cross-Correlation, cross-correlation (C) values $C_{i,j}(\tau)$ between pairs $(x_i, x_j)$ of EEG channels $x_i(t)$ and $x_j(t)$ are computed at delays $\tau$ which can range from −0.5 seconds to 0.5 seconds, in order to account for the propagation and processing time of brainwaves, and the maximal value of such cross-correlation values is retained, as in:

$$C_{a,b} = \max_\tau \left\{ \left| \frac{C_{a,b}(\tau)}{\sqrt{C_a(0) \cdot C_b(0)}} \right| \right\} \text{ where} \quad \text{(Eq. 1)}$$

$$C_{a,b}(\tau) = \begin{cases} \frac{1}{N-\tau} \sum_{i=1}^{N-\tau} x_a(t+\tau)x_b(\tau) & \tau \geq 0 \\ C_{b,a}(-\tau) & \tau < 0 \end{cases}$$

and N is the number of time points within the analysis window.

A first exemplary nonlinear measure can be Nonlinear Interdependence, which measures the distance, in state-space, between time-delay embedded trajectories of two EEG channels. Nonlinear interdependence (S) can be a bivariate feature that measures the Euclidian distance, in reconstructed state-space, between trajectories described by two EEG channels $x_a(t)$ and $x_b(t)$.

First, e.g., each exemplary EEG channel x(t) is time delay-embedded into a local trajectory x(t), using delay $\tau=6$ (approximately 23 ms) and embedding dimension d=10:

$$x(t) = \{x(t-(d-1)\tau), \ldots, x(t-\tau), x(t)\} \quad \text{(Eq. 2)}$$

After time-delay embedding of EEG waveforms into respective sequences of vectors $x_a(t)$ and $x_b(t)$, the non-symmetric statistic $S(x_i|x_j)$ can be computed using the following:

$$S(x_a|x_b) = \frac{1}{N} \sum_{t=1}^{N} \frac{R(t, x_a)}{R(t, x_a|x_b)} \quad \text{(Eq. 3)}$$

where the distance of $x_a(t)$ to its K nearest neighbors in state space can be defined as (Eq. 4) and the distance of $x_a(t)$ to the K nearest neighbors of $x_b(t)$ in state space can be defined as (Eq. 5):

$$R(t, x_a) = \frac{1}{K} \sum_{k=1}^{K} \|x_a(t) - x_a(t_k^a)\|_2^2 \quad \text{(Eq. 4)}$$

$$R(t, x_a|x_b) = \frac{1}{K} \sum_{k=1}^{K} \|x_a(t) - x_a(t_k^b)\|_2^2 \quad \text{(Eq. 5)}$$

where:
$\{t_1^a, t_2^a, \ldots, t_K^a\}$ are the time indices of the K nearest neighbors of $x_a(t)$; and
$\{t_1^b, t_2^b, \ldots, t_K^b\}$ are the time indices of the K nearest neighbors of $x_b(t)$.

The exemplary nonlinear interdependence feature is a symmetric measure:

$$S_{a,b} = \frac{S(x_a|x_b) + S(x_b|x_a)}{2} \quad \text{(Eq. 6)}$$

The second exemplary nonlinear measure, also called Dynamical Entrainment, can be based on the measure of chaos in the EEG. Such exemplary measure can estimate from any two observed time-series, the difference of their largest Lyapunov exponents, i.e., the exponential rates of growth of an initial perturbation.

The difference of short-term Lyapunov exponents (DSTL), which can be referred to dynamical entrainment, can be based on Chaos theory. First, the largest short-time Lyapunov coefficients $STL_{max}$ on each EEG channel x(t) can be estimated by using moving windows on time-delay embedded time-series x(t). $STL_{max}$ can be a measure of the average exponential rates of growth of perturbations $\delta x(t)$ $$STL_{max}(x) = \frac{1}{N\Delta t} \sum_{t=1}^{N} \log_2 \left| \frac{\delta x(t+\Delta t)}{\delta x(t)} \right| \quad \text{(Eq. 7)}$$

where $\Delta t$ is the time after which the perturbation growth is measured. Positive values of the largest Lyapunov exponent can be an indication of a chaotic system, and this exponent can increase with unpredictability. In an exemplary measurement, where EEG is sampled at 256 Hz, the time delay is $\tau=6$ samples or 20 ms, embedding dimension is d=7 and evolution time $\Delta t=12$ samples or 47 ms. The exemplary bivariate feature can be the difference of $STL_{max}$ values between any two channels:

$$DSTL_{a,b} = |STL_{max}(x_a) - STL_{max}(x_b)| \quad \text{(Eq. 8)}$$

A third exemplary nonlinear bivariate measure that can take advantage of the frequency content of EEG signals is phase synchronization. Two equivalent techniques can be employed to extract the frequency-specific phase of EEG signal: bandpass filtering followed by Hilbert transform or Wavelet transform. Then, statistics on the difference of phases between two channels (such as phase-locking synchrony) can be computed for specific combinations of channels and frequencies.

In wavelet analysis measures of synchrony, first, e.g., frequency-specific and time-dependent phase $\phi_{i,f}(t)$ and $\phi_{j,f}$ (t) can be extracted from the two respective EEG signals $x_i(t)$ and $x_j(t)$ using wavelet transform. Then, three types of statistics on these differences of phase can be computed: phase-locking synchrony SPLV (Eq. 9), entropy H of the phase difference (Eq. 10) and coherence Coh. For instance, phase-locking synchrony SPLV at frequency f is:

$$SPLV_{a,b}(f) = \left| \frac{1}{N} \sum_{t=1}^{N} e^{i(\phi_{a,f}(t) - \phi_{b,f}(t))} \right| \qquad (\text{Eq. 9})$$

$$H_{a,b}(f) = \frac{\ln(M) - \sum_{m=1}^{M} p_m \ln(p_m)}{\ln(M)} \qquad (\text{Eq. 10})$$

where $p_m = \Pr[(\phi_{a,f}(t) - \phi_{a,f}(t)) \in \Phi_m]$ is the probability that the phase difference falls in bin m and M is the total number of bins.

Synchrony can be computed and averaged in seven different frequency bands corresponding to EEG rhythms: delta (below 4 Hz), theta (4-7 Hz), alpha (7-13 Hz), low beta (13-15 Hz), high beta (14-30 Hz), low gamma (30-45 Hz) and high gamma (65-120 Hz), given that the EEG recordings used are sampled at 256 Hz. Using seven different frequency bands can increase the dimensionality of 60-frame, 15-pair synchronization patterns from 900 to 6300 elements.

Exemplary Feature Classification for Seizure Prediction

Once univariate or bivariate, linear or nonlinear measurements are derived from EEG, a binary classification of a single variable can be performed, e.g., using a computing arrangement. An exemplary hypothesis is likely that there should be a preictal increase or decrease in the values of an EEG-derived feature. Statistical methods can have a posteriori and in-sample tuning of a binary classification threshold (e.g. pre-ictal vs. interictal) on an unique measure extracted from EEG.

The usage of a simple binary threshold can have limitations. For example, it may not facilitate the use of high-dimensional features. By contrast, machine learning theory (sometimes also called statistical learning theory) can handle high-dimensional and spatio-temporal data, as illustrated in countless applications such as video or sound recognition.

Importantly, machine learning can provide high-dimensional and spatio-temporal data with a methodology for learning by example from data, and for quantifying the efficiency of the learning process. The available data set can be divided into a training set ("in-sample") and a testing set ("out-of-sample"). Using the computing arrangement, an exemplary training can iteratively adjust the parameters of the machine in order to minimize the empirical error made on in-sample data, and a theoretical risk related to the complexity of the machine (e.g., number of adjustable parameters). The training set can be further subdivided into training and cross-validation subsets, so that training is stopped before over-fitting when the cross-validation error starts to increase.

In exemplary machine learning procedures, feed-forward Neural Networks (NN) can learn a mapping between multi-dimensional inputs and corresponding targets. The architecture of a neural network can be an ensemble of interconnected processing units or arrangements, organized in successive layers. Learning can comprise tuning the connection weights by back-propagating the gradient of classification errors through the layers of the NN.

Convolutional networks can be a further exemplary specialized architecture able to extract distortion-invariant patterns, such as for handwriting recognition. One such convolutional network architecture, which can be called LeNet5, is currently used in the verification of handwriting on most bank checks in the United States, and has been more recently shown to allow autonomous robot navigation from raw images coming from two (stereoscopic) cameras. This neural network successfully learnt a large collection of highly noisy visual patterns and was capable of avoiding obstacles in unknown terrain. Convolutional networks likely have not been used for the classification of any type of medical data, e.g., physiological data relating to seizures.

Another exemplary machine learning procedure used for multi-dimensional classification is called Support Vector Machines (SVM). SVMs can use the computing arrangement to first compute a metric between all training examples, e.g., called the kernel matrix, and then learn to associate a right target output to a given input, by solving a quadratic programming problem.

Machine learning techniques can be applied mostly to select subsets of features and corresponding EEG channels for further statistical classification. Examples of such algorithms for channel selection included Quadratic Programming, K-means, and Genetic Optimization. In an exemplary machine learning procedure for seizure prediction, raw EEG time series and their wavelet transform coefficients can be fed into a Recurrent Neural Network (RNN), i.e., a neural network that maintains a "memory" of previous inputs and thus learns temporal dependencies between. The RNN can be trained to classify each EEG channel separately as being in an interictal or preictal state.

Exemplary Methods

Exemplary methods for seizure prediction methodology can be performed using the computing arrangement and can include: selection of training and testing data, as well as EEG filtering, computation of bivariate features of EEG synchronization, aggregation of features into spatio-temporal, or spatio-temporal and frequency-based patterns, machine learning-based optimization of a classifier that inputs patterns of bivariate features and outputs the preictal or interictal category and retrospective sensitivity analysis to understand the importance of each EEG channel and frequency band within the patterns of features.

Exemplary Data and Preprocessing

Exemplary data was used from the publicly available EEG database at the Epilepsy Center of the University Hospital of Freiburg, Germany (https://epilepsy.uni-freiburg.de/freiburg-seizure-prediction-project/eeg-database/), containing invasive EEG recordings of 21 patients suffering from medically intractable focal epilepsy. Previous analysis of this dataset yielded at best a seizure prediction performance of 42% sensitivity and an average of 3 false positives per day. Such exemplary EEG data had been acquired from intracranial grid-electrodes, strip-electrodes, and depth-electrodes at a 256 Hz sampling rate, and digitized to 16 bit by an analogue-to-digital converter. In the source dataset, a certified epileptologist had previously restricted the EEG dataset to, e.g., 6 channels, from three focal electrodes (13) involved in early ictal activity, and three electrodes (e.g., 46) not involved during seizure spread.

Each of the patients' EEG recordings from the Freiburg database contained between, e.g., 2 and 6 seizures and at least about 50 minutes of pre-ictal data for most seizures, as well as approximately 24 hours of EEG-recordings without seizure activity and spanning the full wake-sleep cycle.

According to the exemplary techniques according to the present disclosure using which the experiments have been performed, preictal samples preceding the last 1 or 2 seizures (depending on that patient's total number of seizures) and about 33% of the interictal samples were set apart. The remaining samples were training (in-sample) data. Further, 10% or 20% of training data were randomly selected for cross-validation. The training procedure can be stopped either after a fixed number of iterations, or cross-validation data was used to select the best model (and stop the training procedure prematurely). In summary, the classifiers were trained on the earlier seizures and on wake-sleep interictal data, and these same classifiers were evaluated on later seizures and on different wake-sleep interictal data.

In these exemplary techniques, Infinite Impulse Response (IIR) elliptical filters were applied, using code from EEGLab to clean some artifacts: a 49-51 Hz band-reject $12^{th}$-order filter to remove power line noise, a 120 Hz cutoff low-pass $1^{st}$-order filter, and a 0.5 Hz cutoff high-pass $5^{th}$-order filter to remove the dc component. All data samples were scaled on a per patient basis, to either zero mean and unit variance (for logistic regression and convolutional networks) or between −1 and 1 (for support vector machines). Here, $x_i(t)$ denotes the time series representing the i-th channel of the preprocessed EEG.

Exemplary Extraction of Bivariate Features

A bivariate feature can be a measure of a certain relationship between two signals. Bivariate features can be computed on 5 second windows (N=1280 samples at 256 Hz) of any two EEG channels $x_a$ and $x_b$. For EEG data having M channels, features on M×(M−1)/2 pairs of channels (e.g. 15 pairs for M=6 in the Freiburg EEG dataset) can be computed. Some features can be specific to a frequency range.

Various types of bivariate features can be used. In a first exemplary bivariate feature, cross-correlation C, a linear measure of dependence between two signals that also facilitates fixed delays between two spatially distant EEG signals to accommodate potential signal propagation can be used. In a second exemplary bivariate feature, nonlinear interdependence S, which measures the distance in state-space between the trajectories of two EEG channels can be used. In a third exemplary bivariate feature, dynamical entrainment DSTL, i.e., the difference of short-term Lyapunov exponents, based on a common measure of the chaotic nature of a signal can be used. By estimating, from two time-delay embedded time-series, the difference in the exponential rate of growth of an initial perturbation between those two signals, the dynamical entrainment feature quantifies the convergence of chaotic behavior of the epileptic brain as it transits from the interictal to ictal state. The last three exemplary features that can be used are based on phase synchrony. First, frequency-specific and time-dependent phase $\phi_{a,f}(t)$ and $\phi_{b,f}(t)$ were extracted from the two respective EEG signals $x_a(t)$ and $x_b(t)$ using Wavelet Transform. Then, three types of statistics on the difference of phases between two channels can be made: phase-locking synchrony SPLV, entropy H of the phase difference and coherence Coh.

Exemplary Aggregation of Bivariate Features into Spatio-Temporal Patterns

An exemplary pattern can be a structured collection of features. The exemplary pattern can group features along the spatial, time and frequency dimensions. Two-dimensional (2-D) patterns can be formed by aggregating features from all 15 pairs of channels (across rows) and over several consecutive time frames (across columns). Specifically, 1 minute or 5 minute long patterns, having 12 or 60 frames, respectively, can be formed. In the case of frequency-based features, patterns can be stacked, row-wise and from all frequency ranges, into one pattern.

FIG. 1(a) shows an example of a 1-minute EEG recording (upper panel) and its corresponding pattern of cross-correlation features (lower panel) for interictal recordings for a particular patient. FIG. 1(b) shows an example of a 1-minute EEG recording (upper panel) and corresponding pattern of cross-correlation features (lower panel) for preictal recordings for the same patient. Exemplary EEG was acquired on M=6 channels. Cross-correlation features were computed on 5 second windows and on p=M×(M−1)/2=15 pairs of channels. Each exemplary pattern contains 12 frames of bivariate features (1 min).

As shown in FIGS. 1(a) and 1(b), the dimensionality of exemplary feature patterns can range from 180 (e.g., cross-correlation on approximately 1 minute windows) to 6300 (e.g., wavelet phase-locking synchrony on approximately 5 minute windows). The approximately-5-minute long patterns achieved better results to the approximately-1-minute-long patterns, and the seizure prediction results discussed herein are based on approximately 5 minute long patterns only.

For example, $y_t$ can denote a pattern at time t (i.e., a sample of bivariate features), and $z_t$ can be denoted the associated label (−1 for preictal, 1 for interictal). Further, $y_t$ can either be one long vector or a matrix indexed by time and by channel pair and frequency band.

Exemplary Machine Learning Classification of Patterns of Bivariate Features

Exemplary bivariate patterns $y_t$ that represent a "snapshot" of EEG synchronization around time t were input into a decision system that would classify them as preictal or interictal. The parameters of that classifier were learned on the training subset of the dataset using machine learning. For example, $z_t$ can note the label of pattern $y_t$ (−1 for preictal, 1 for interictal) and $\bar{z}_t$ can note the output of the classifier. Although three different types of classifiers can be used, with their respective machine learning algorithms, all training algorithms had in common minimizing, for every training sample $y_t$, the error between output $\bar{z}_t$ and target $z_t$. The error between the output and the target can be one term of the loss function: regularization. Test data can be set apart during the training phase, e.g., the performance of the classifiers on out-of-sample data can be validated.

A first exemplary classifier tested can be logistic regression, parameterized by weights w and bias b (see Eq. 11), and optimized by minimizing loss function (see Eq. 12). This exemplary classifier can perform a dot product between pattern $y_t$ and weight vector w, and add the bias term b. The positive or negative sign of the result (see Eq. 11) can be used (e.g., using the computing arrangement) to decide whether pattern $y_t$ is interictal or preictal. By consequence, this algorithm can be qualified as a linear classifier. Indeed, each feature $y_{t,i}$ of the pattern can be associated its own weight $w_i$ and the dependency is linear. Exemplary weights w and bias b can be adjusted during the learning phase, through stochastic gradient descent.

$$\bar{z}_t = \text{sign}(w^T y_t + b) \quad \text{(Eq. 11)}$$

$$L(y_t, z_t, w, b) = 2 \log(1 + e^{-z_t(w^T y_t + b)}) + \lambda |w| \quad \text{(Eq. 12)}$$

A second exemplary classifier tested was built on convolutional networks. Convolutional networks can be trainable, multi-layer, non-linear systems that are specifically designed to extract and classify high-dimensional patterns from images or multivariate time-series. Convolutional networks can be seen as multi-layer neural networks in which each layer is a bank of finite-impulse response filters followed by point-wise sigmoid squashing functions. A parallel can be made between convolutional networks and an extremely simplified model of the V1 visual cortex, because each layer processes locally inputs from the previous layer, and because this processing is replicated over all the input pattern. All the layers are trained simultaneously using a version of the back-propagation learning algorithm. They can learn low-level features and high-level representations in an integrated manner. A main advantage of convolutional networks is that they can learn optimal time-invariant local feature detectors from input matrix $y_t$ (which is indexed by time) and can thus build representations that are robust to time shifts of specific feature motifs.

Figure 2:
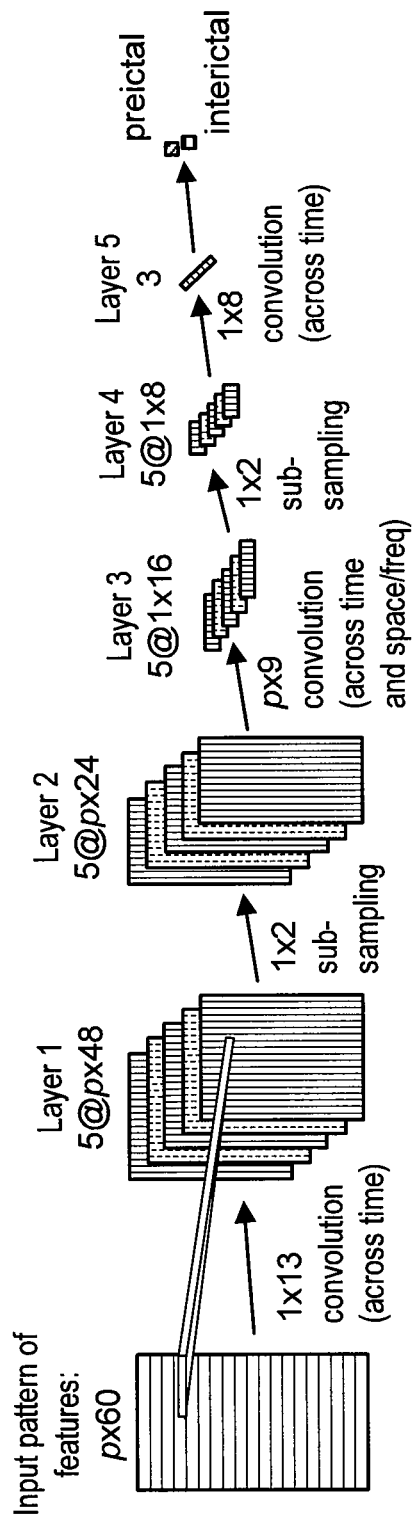
FIG. 2 is an illustration of an exemplary convolutional network architecture having a stack of 5 layers of neural network connections.

FIG. 2 shows an exemplary convolutional network used for the classification of patterns of bivariate features containing, e.g., 60 consecutive frames (e.g., 5 minutes) of p simultaneous features. In FIG. 2, a specific convolutional network architecture having a stack of 5 layers of neural network connections (also called weight layers) is shown. Weight layers 1, 3 and 5 are convolutional layers, and layers 2 and 4 are subsampling layers. Each layer can be used to compute a weighted sum over a "local" subset of inputs. In an exemplary embodiment, p can be the number of pairs of channels (15) times the number of frequency bands (1 or 7). Then, 12-frame patterns (i.e., 1 minute long) can be processed as follows. For example, Layer 1 can perform 5 different 5-point convolutions over the time dimension; Layer 3 can perform 5 different 3-point convolutions over time and p-point convolutions over all channels and frequency bands; and Layer 5 can be fully connected between all its inputs (i.e. the outputs of Layer 4) and the 2 output nodes (one for "preictal" and one for "interictal"). Layer 2 and Layer 4 can average two consecutive time points (i.e., subsampled in time). 60-frame patterns (i.e., 5 minute long) were processed slightly differently: Layer 1 can perform 5 different 13-point convolutions over the time dimension; and Layer 3 can perform 5 different 9-point convolutions over time and p-point convolutions over all channels and frequency bands. For example, 5 minute long patterns achieved superior seizure prediction results to 1 minute long patterns. 2 output nodes can be chosen because it enabled an asymmetric learning that penalized more false positives (false preictal alarms) than false negatives (missed preictal alarms).

Convolutional networks can be a deep neural network architecture with a small number of parameters (weights) that are replicated over large patterns. Convolutional networks can behave similar to successive arrays of small convolution filters. Inputs to hidden layers 1, 3 and 5 result from convolutions and inputs to hidden layers 2 and 4 are results from subsampling. Computations performed between hidden layer 5 and an output layer of the convolutional networks correspond to a low-dimensional linear classifier. Due to alternated convolutional and subsampling layers, filters on the first hidden layer cover small areas of the input pattern, while filters on layers 3 and 5 cover increasingly larger areas of the original input pattern. For the specific problem of seizure prediction, convolutions are done only across time, with the exception of layer 3, which convolves input from all pairs of channels and all frequencies. Layer 1 can be seen as a simple short time pattern extractor, while layers 3 and 5 can perform highly nonlinear spatio-temporal pattern recognition. For M=6 EEG channels, $p=M \times (M-1)/2=15$ channels for non-frequency-based features, and $p=M \times (M-1)/2 \times 7=105$ channels for wavelet synchrony-based features computed on 7 frequency bands.

The two exemplary neural network architectures (logistic regression, linear, and convolutional networks, highly non-linear) can then be compared with a third type of classifier, called Support-Vector Machines (SVM). SVM are pattern matching-based classifiers that compare any input pattern $y_t$ to a set of support vectors $y_s$. Exemplary support vectors can be a subset of the training dataset and are chosen during the training phase. The function used to compare two patterns $y_t$ and $y_s$ is called the kernel function $K(y_t, y_s)$ (Eq. 13). The decision function (Eq. 14) can be a weighted combination of the kernel functions. In this study, SVMs with Gaussian kernels were used (Eq. 13). The set S of support vectors $y_s$, the Lagrange coefficients α and bias b were optimized using Quadratic Programming. Gaussian standard deviation parameter γ and regularization parameter were selected by cross-validation over a grid of values. The whole classifier and training algorithm had been implemented with the LibSVM library.

$$K(y_t,y_s)=\exp(-(y_t-y_s)^2/\gamma) \quad \text{(Eq. 13)}$$

$$\bar{z}_t=\text{sign}(\Sigma_{s \in S}\alpha_s K(y_t,y_s)+b) \quad \text{(Eq. 14)}$$

Exemplary Feature Selection

Exemplary training procedures for neural network classifiers such as logistic regression and convolutional networks can facilitate a regularization term to be added on the weights (parameters) w. For example, regularization can be minimizing the norm of vector w. Specifically, e.g., an L1-norm (sum of absolute values) regularization term can be added to the loss function (Eq. 12) that is minimized during gradient descent. Typically, a value of 0.001 for lambda can be used. This L1 term uniformly can pull the weights towards zero during gradient-based optimization. Accordingly, e.g., only a subset $\{w_i\}$ of these weights "survive", and the final solution w* contains a minimal set of weights that simultaneously minimizes the error on the training dataset. Such exemplary L1-norm weight selection is also called the "LASSO" procedure, which is used as a task-specific way to select features, as opposed to a task-agnostic selection of features prior to the training algorithm (i.e., the only non-zero (or non-negligible) features are the ones that specifically discriminate between interictal and preictal patterns of that given patient).

After training the neural network, a sensitivity analysis on the inputs can be performed to see which features were important for the discrimination. In the case of Logistic Regression, individual weights $w_i$ are used. For convolutional networks, the gradients obtained for each testing sample onto the inputs can be back-propagated, and then the squares of these gradients on inputs may be summed.

Exemplary Results

Exemplary high-dimensional spatio-temporal patterns of bivariate features allow for better separation between interictal and preictal recordings. For results obtained with machine learning-trained classifiers, for each patient, at least one method predicted 100% of the seizures on the test dataset, on average of, e.g., about 60 minutes before the onset and without false alarm. Exemplary neural network-based classifiers enable a-posteriori selection of channels and frequency bands relevant for seizure prediction.

Exemplary Increased Separability of Patterns Instead of Individual Features

As an initial matter, exemplary discriminative power of patterns of features can be compared to individual features, e.g., using the computing arrangement. A pattern can aggregate features across successive time frames and over all pairs of EEG channels. By comparing between exemplary patterns across channels versus patterns across time and channels, the benefit of adding the time dimension to patterns can be assessed.

An exemplary Principal Component Analysis (PCA) of patterns of bivariate features with different lengths of aggregation can be performed across time. Spatial patterns (e.g., 1 single time-frame, where features have been computed on a 5 second window), short spatio-temporal patterns (e.g., 12 time-frames covering 1 minute) and long spatio-temporal patterns (60 time-frames covering 5 minutes) can be determined. To account for variability between patients, the PCA can be performed individually for each patient and for each type of feature (cross-correlation, nonlinear interdependence, difference of Lyapunov exponents, phase-locking value, wavelet coherence and entropy of phase difference). The projections of all the interictal, preictal and ictal/postictal patterns along their first two principal components can be visually inspected. The top PCA components corresponded to the directions of the highest variability of the feature values. The 2-D projections of preictal and interictal 1-frame patterns overlapped considerably, more than the projections of, e.g., 12-frame or 60-frame patterns.

Figure 3:
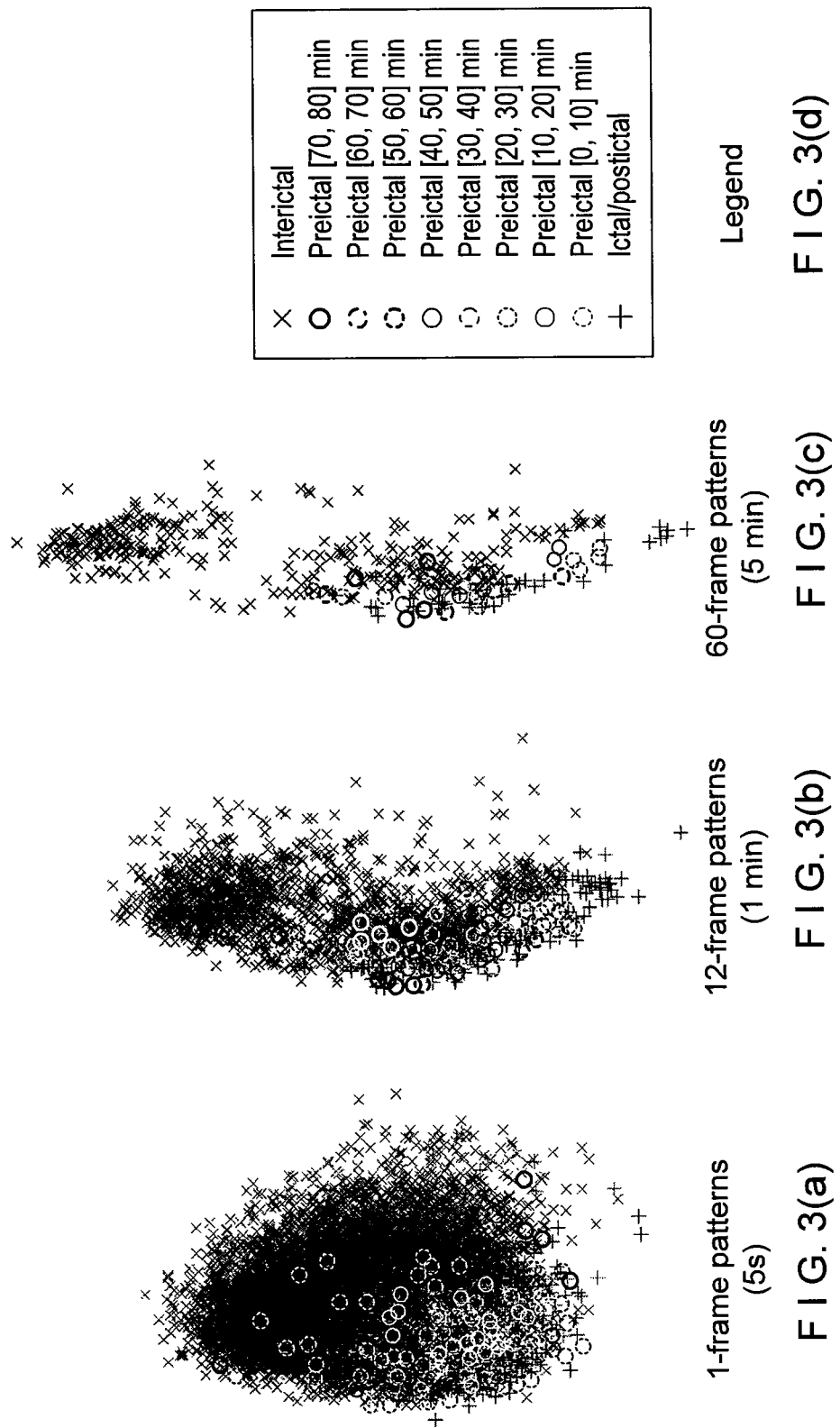
FIG. 3a is an illustration of an exemplary graph of a Principal Component Analysis projection of 1-frame patterns of phase-locking synchrony values for a patient.
FIG. 3b is an illustration of an exemplary graph of a Principal Component Analysis projection of 12-frame patterns of phase-locking synchrony values for a patient.
FIG. 3c is an illustration of an exemplary graph of a Principal Component Analysis projection of 60-frame patterns of phase-locking synchrony values for a patient.
FIG. 3d is a legend associated with the exemplary graphs of FIGS. 3a-3c.

An exemplary illustration of such phenomenon is shown in FIGS. 3(a)-3(c), which shows the exemplary PCA projection of patterns of phase-locking synchrony values for a patient. As shown in FIG. 3(a), it is difficult to see a boundary between the interictal and preictal clusters of 1-frame patterns (5 second) (without time aggregation). (See legend of FIG. 3(d)). The boundary becomes more apparent for time-aggregated 12-frame (1 minute) patterns in FIG. 3(b), and even more apparent for 60-frame patterns (5 minute) as shown in FIG. 3(c). The patterns in FIG. 3(a) are vectors containing 15×7=105 elements (15 pairs of channels times 7 frequency bands), the patterns in FIG. 3(b) are (15×7)×12 matrices containing 1260 elements, and the patterns in FIG. 3(c) are, e.g., (15×7)×60 matrices containing 6300 elements. As the duration (number of frames) of patterns increases, the separation between the preictal and interictal patterns becomes more apparent, which can explains why a simple linear classifier (logistic regression) obtained good seizure prediction results on 60-frame patterns.

This observation about spatio-temporal patterns was empirically confirmed, since seizure prediction performance was superior for 5 minute long patterns than for 1 minute long patterns. Accordingly, later results are obtained using, e.g., 5 minute long patterns.

Exemplary Classification Results

Figure 4:
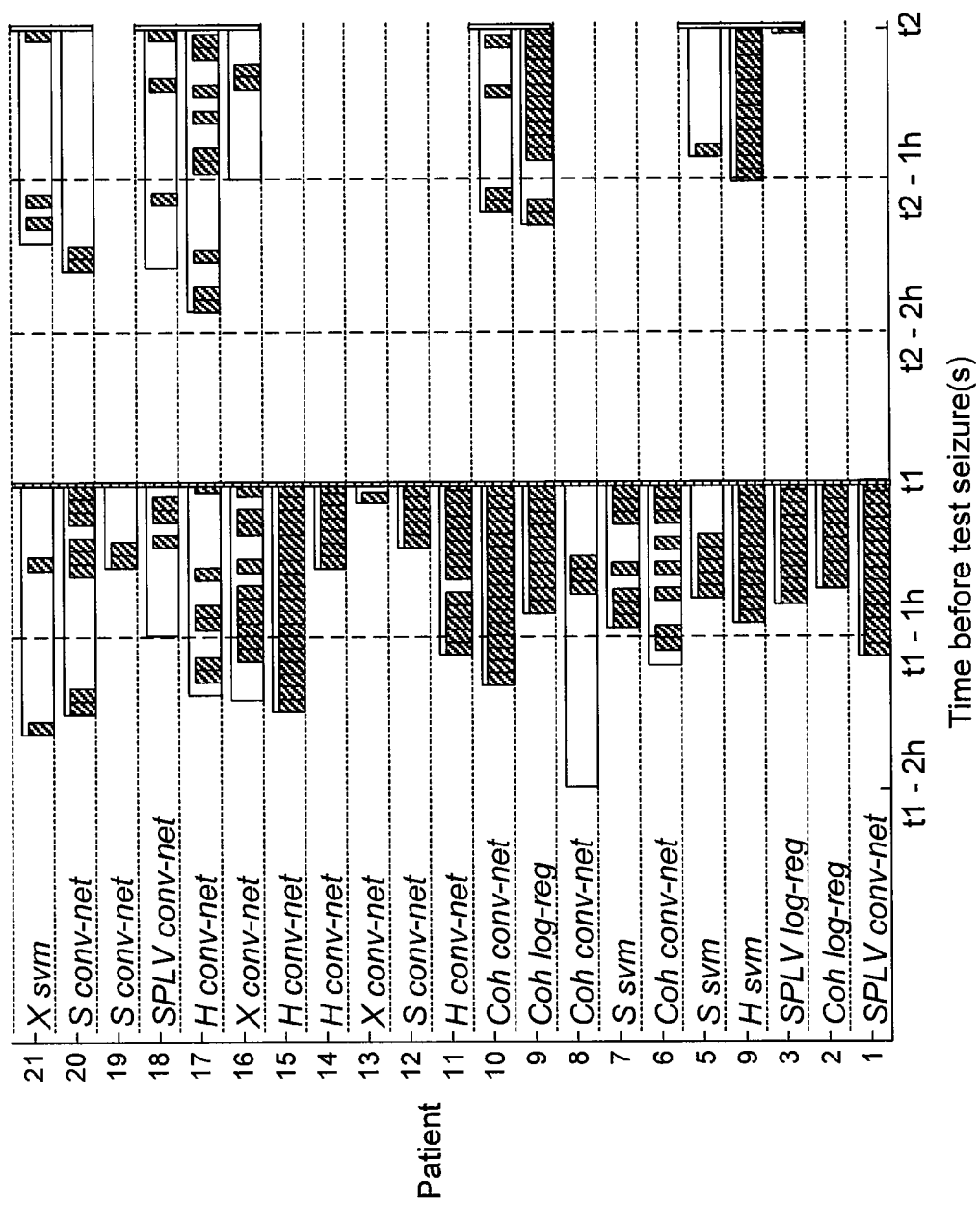
FIG. 4 is an illustration of an exemplary graph showing exemplary times of preictal alarms for patients.

FIG. 4 shows an illustration of an exemplary graph showing exemplary times of preictal alarms for each patient, achieved using exemplary patient-specific methods. For each patient (e.g., Patients numbered 1-21 on the vertical axis), FIG. 4 shows a total duration of preictal EEG recordings before each test seizure, and the times of preictal alarms (horizontal axis). Some patients had one seizure used for the test, other patients had two seizures, depending on the total number of seizures available for that patient in the dataset. The type of bivariate features and classifier are indicated on the vertical axis next to the patient number.

For each patient, at least one method predicted 100% of the test seizures, on average 60 minutes before the onset and with no false alarm. As shown in FIG. 4, the only exception was patient 13 that had only 10 min of preictal EEG for the test seizure, and where an "alarm" was obtained 7 minutes before the onset of the seizure. Because an important goal of seizure prediction is the epileptic patient's quality of life, classification performance can be measured in terms of false alarms per hour and sensitivity, i.e., number of seizures where at least one preictal sample is classified as such.

The exemplary seizure prediction methods investigated were a combination of one type of feature patterns (cross-correlation C, nonlinear interdependence S, difference of Lyapunov exponents DSTL, phase-locking synchrony SPLV, entropy of phase difference H and distribution or wavelet coherence Coh) and one type of classifier (Logistic Regression log reg, convolutional networks lenet5 or SVM).

TABLE 1

| | Type of bivariate features | | | | | |
| --- | --- | --- | --- | --- | --- | --- |
| | No frequency information | | | Frequency-based | | |
| | C | S | DSTL | SPLV | H | Coh |
| Perfect seizure prediction (test set) | 11 | 19 | 2 | 14 | 11 | 13 |

Table 1 is an exemplary chart showing a number of patients with perfect seizure prediction results on a test dataset, as a function of the type of EEG feature.

TABLE 2

| | Type of classifier | | |
| --- | --- | --- | --- |
| | log reg | conv net | svm |
| Perfect seizure prediction (test set) | 14 | 20 | 11 |

Table 2 is an exemplary chart showing a number of patients with perfect seizure prediction results on a test dataset, as a function of the type of classifier.

TABLE 3

| | | pat 1 | | pat 2 | | pat 3 | | | pat 4 | | | pat 5 | | | pat 6 | | pat 7 | | pat 8 | |
| --- | --- | --- | --- | --- | --- | --- | --- | --- | --- | --- | --- | --- | --- | --- | --- | --- | --- | --- | --- | --- |
| feature | assifier | fpr | ts1 | fpr | ts1 | fpr | ts1 | ts2 | fpr | ts1 | ts2 | fpr | ts1 | ts2 | fpr | ts1 | fpr | ts1 | fpr | ts1 |
| C | g reg | | | | | | | | | | | | | | | | | | 0 | 46 |
| | conv net | 0 | 68 | 0 | 40 | | | | 0 | 54 | 61 | 0 | 25 | 52 | | | 0 | 56 | | |
| | svm | 0.2 | 68 | 0 | 40 | | | | | | | | | | 0.1 | 66 | 0 | 36 | | |
| S | g reg | | | | | 0 | 48 | 3 | 0 | 54 | 61 | | | | | | 0 | 56 | | |
| | conv net | 0 | 68 | 0 | 40 | 0 | 48 | 3 | 0 | 54 | 61 | | | | | | 0 | 56 | | |
| | svm | 0.2 | 68 | 0 | 40 | | | | 0.1 | 39 | 61 | 0 | 45 | 52 | 0.1 | 16 | 0 | 56 | 0 | 9 |
| DSTL | svm | | | | | | | | 0 | 39 | 51 | | | | | | | | | |

TABLE 3-continued

| | feature assifier | | | | | | | | | | | | | | | | | | | | | | |
|---|---|---|---|---|---|---|---|---|---|---|---|---|---|---|---|---|---|---|---|---|---|---|---|
| SPLV | g reg | 0 | 68 | 0 | 40 | 0 | 48 | 3 | 0 | 54 | 61 | | | | 0 | 66 | 0 | 56 | | |
| | conv net | 0 | 68 | 0 | 40 | 0 | 48 | 3 | 0 | 54 | 61 | | | | | 0 | 56 | 0 | 39 |
| | svm | 0.1 | 68 | 0 | 40 | 0 | 48 | 3 | 0 | 54 | 41 | | | | 0.1 | 66 | 0 | 56 | | |
| H | g reg | | | 0 | 40 | 0 | 48 | 3 | 0 | 54 | 61 | | | | 0 | | 0 | 56 | | |
| | conv net | 0 | 68 | 0 | 40 | 0 | 48 | 3 | 0 | 54 | 61 | | | | | 0 | 56 | | |
| | svm | 0.2 | 68 | 0 | 40 | 0 | 48 | 3 | 0 | 54 | 61 | | | | 0.1 | 66 | 0 | 56 | | |
| Coh | g reg | 0 | 68 | 0 | 40 | 0 | 48 | 3 | 0 | 54 | 61 | | | | 0 | 66 | 0 | 56 | | |
| | conv net | 0 | 68 | 0 | 40 | 0 | 48 | 3 | 0 | 54 | 61 | 0 | 45 | 52 | 0 | 71 | 0 | 56 | 0 | 44 |
| | svm | 0.1 | 68 | 0 | 40 | 0 | 48 | 3 | 0 | 54 | 61 | | | | 0.1 | 66 | 0 | 56 | | |

| | | pat 9 | | | pat 10 | | | pat 11 | | | pat 12 | | pat 13 | | pat 14 | | pat 15 | | pat 16 | | |
|---|---|---|---|---|---|---|---|---|---|---|---|---|---|---|---|---|---|---|---|---|---|
| feature | assifier | fpr | ts1 | ts2 | fpr | ts1 | ts2 | fpr | ts1 | ts2 | fpr | ts1 | fpr | ts1 | fpr | ts1 | fpr | ts1 | fpr | ts1 | ts2 |
| C | g reg | | | | 0 | 79 | 73 | | | | 0 | 25 | 0 | 2 | | | | | | | |
| | conv net | | | | | | | | | | 0 | 25 | 0 | 7 | | | | | 0 | 65 | 25 |
| | svm | | | | 0.1 | 79 | 73 | | | | 0 | 25 | | | | | | | 0 | 60 | 20 |
| S | g reg | | | | | | | | | | 0 | 25 | | | | | | | | | |
| | conv net | 0 | 51 | 78 | | | | 0 | 67 | | 0 | 25 | | | | | | | | | |
| | svm | 0.1 | 51 | 43 | 0.1 | 79 | 73 | 0.3 | 67 | | | | | | 0.1 | 33 | 0.1 | 90 | 0 | 55 | 55 |
| DSTL | svm | | | | 0.2 | 9 | 3 | | | | | | | | | | | | | | |
| SPLV | g reg | 0 | 51 | 78 | | | | 0 | 57 | | 0 | 25 | | | | | | | | | |
| | conv net | 0 | 51 | 78 | 0 | 79 | 73 | 0 | 67 | | 0 | 25 | | | | | 0 | 90 | | | |
| | svm | 0 | 51 | 78 | 0.2 | 79 | 73 | 0 | 27 | | | | | | 0.3 | 33 | 0 | 80 | | | |
| H | g reg | 0 | 51 | 78 | | | | 0 | 67 | | 0 | 25 | | | 0 | 33 | 0 | 70 | | | |
| | conv net | 0 | 51 | 78 | | | | 0 | 67 | | 0 | 25 | | | 0 | 33 | 0 | 90 | | | |
| | svm | 0 | 51 | 78 | 0.2 | 79 | 73 | 0 | 27 | | | | | | 0.1 | 33 | 0 | 85 | | | |
| Coh | g reg | 0 | 51 | 78 | | | | 0 | 37 | | 0 | 25 | | | | | 0 | 45 | 0 | 60 | 10 |
| | conv net | 0 | 51 | 78 | 0 | 79 | 73 | 0 | 67 | | 0 | 25 | | | | | 0 | 90 | | | |
| | svm | 0 | 51 | 78 | 0.2 | 79 | 73 | 0 | 32 | | | | | | 0.3 | 28 | 0 | 85 | 0 | 60 | 5 |

| | | | pat 17 | | | pat 18 | | | pat 19 | | pat 20 | | | pat 21 | | |
|---|---|---|---|---|---|---|---|---|---|---|---|---|---|---|---|---|
| | | feature assifier | fpr | ts1 | ts2 | fpr | ts1 | ts2 | fpr | ts1 | fpr | ts1 | ts2 | fpr | ts1 | ts2 |
| | C | g reg | | | | | | | | | 0 | 91 | 96 | | | |
| | | conv net | | | | | | | | | | | | 0.1 | 99 | 70 |
| | | svm | | | | | | | | | | | | | | |
| | S | g reg | | | | | | | 0 | 28 | 0 | 91 | 96 | | | |
| | | conv net | | | | | | | | | | | | | | |
| | | svm | | | | | | | | | | | | | | |
| | DSTL | svm | | | | | | | | | | | | | | |
| | SPLV | g reg | | | | | | | | | | | | 0 | 99 | 75 |
| | | conv net | | | | 0 | 20 | 70 | 0 | 28 | | | | | | |
| | | svm | | | | | | | | | | | | 0.1 | 99 | 80 |
| | H | g reg | | | | | | | | | | | | | | |
| | | conv net | 0 | 78 | ## | | | | | | | | | | | |
| | | svm | | | | | | | | | | | | 0.1 | 14 | 75 |
| | Coh | g reg | | | | 0 | 25 | 90 | | | 0 | 99 | 20 | | | |
| | | conv net | | | | | | | | | | | | | | |
| | | svm | | | | 0.2 | 15 | 90 | | | | | | 0.1 | 99 | 75 |

Table 3 is an exemplary graph showing seizure prediction results on the test dataset, as a function of the type of EEG feature and type of classifier. For each patient, the false positives rate (in false alarms per hour) as well as the time to seizure at the first preictal alarm (in minutes), for one or two test seizures, are indicated. The cross marks indicate combinations of EEG feature type and classifier type that failed to predict the test seizures, or that had more than 0.3 false positives per hour.

Tables 1-3 illustrate how many patients had "perfect prediction" of their test seizures, i.e., zero-false alarm during interictal phases and at least one alarm during pre-ictal phases, given each type of feature pattern (see Table 1) or classifier (see Table 2). Table 3, organized by patient, feature type and classifier, displays a frequency of false alarm per hour, and how many minutes ahead the one or two test seizures were predicted. FIG. 4 shows the times of preictal alarms for each patient, achieved using exemplary patient-specific methods. Convolutional networks achieved a zero-false alarm seizure prediction on 20 patients out of 21, compared to 11 using SVM. A linear classification boundary of logistic regression enabled perfect seizure prediction on 14 patients.

Both for convolutional networks and logistic regression, 100% of training samples (patterns of bivariate features) were correctly classified. The only exceptions were patients 17, 19 and 21, where a larger penalty was allowed for false positives than for false negatives. On these three patients, some false negatives were obtained and no false positive on the training and testing datasets were obtained, while managing to predict all train and test seizures. Accordingly, 100% sensitivity and no false positives on the full 88-seizure Freiburg dataset was obtained.

Exemplary Verification of EEG for Artifacts

An analysis of Table 3 reveals that for a given patient and a given test seizure, most exemplary feature-classifier combinations share the same time of first preictal alarm. Most of these time-aligned first preictal alarms also correspond to a beginning of a preictal recording. Reviewing the original raw EEG, and with the help of a trained epileptologist, additional sanity checks were performed.

First, a verification can be made that there were no recording artifacts that would have helped differentiate interictal from preictal EEG, and second, that exemplary EEG segments corresponding to the pattern at the time of the first preictal alarm were not artifacts either. Through visual inspection, several EEG segments were compared: at the time of the first preictal alarm, right before the seizure and a few randomly chosen 5 minute segments of normal interictal EEG.

There was a high frequency of artifacts on preictal recordings for patients 4 and 7, and that no such artifacts were visible on interictal recordings. For all other patients, short artifacts were indiscriminately present on both preictal and interictal segments. Moreover, sub-clinical events or even seizures on the preictal EEG of patients 3, 4, 6, and 16 were observed. These sub-clinical events were correctly classified as preictal alarms.

Exemplary Feature Selection Results

An additional functionality of the exemplary seizure prediction algorithm is the feature selection mechanism set out above in the "Exemplary Feature Selection." The exemplary feature selection can assist in narrowing the set of input bivariate features. When the parameters of the exemplary logistic regression or convolutional network classifiers (but not the support vector machine) are learned, weight parameters can be driven to zero due to L1-norm regularization, and the few remaining exemplary non-zero parameters can be those that enable successful classification on the exemplary training, cross-validation and testing datasets.

A sensitivity analysis performed on individual classifier inputs can identify which couples of EEG channels were discriminative between preictal and interictal patterns. For example, out of the 15 pairs of exemplary channels, generally only 3 or 4 pairs were actually used for seizure prediction when using non-frequency-based features (cross-correlation C and nonlinear interdependence S). Similarly, only a subset of frequency bands was discriminatory for seizure prediction classification when using exemplary wavelet-analysis based measures of synchrony (phase-locking SPLV, coherence Coh or entropy H).

Figure 5A:
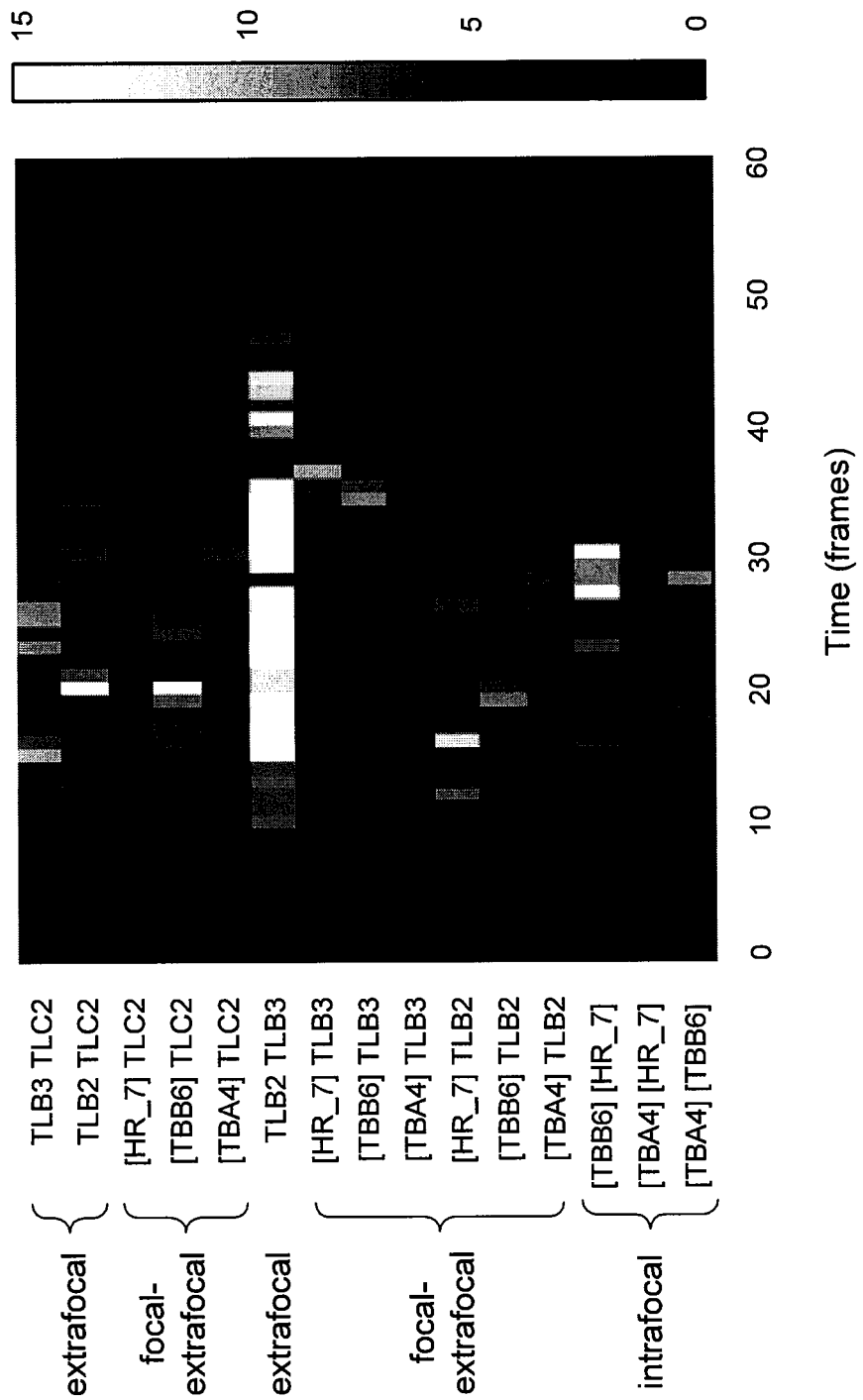
FIG. 5a is an illustration of an exemplary graph that represents an input sensitivity of convolutional networks performed on 5 minute patterns of nonlinear interdependence.
Figure 5B:
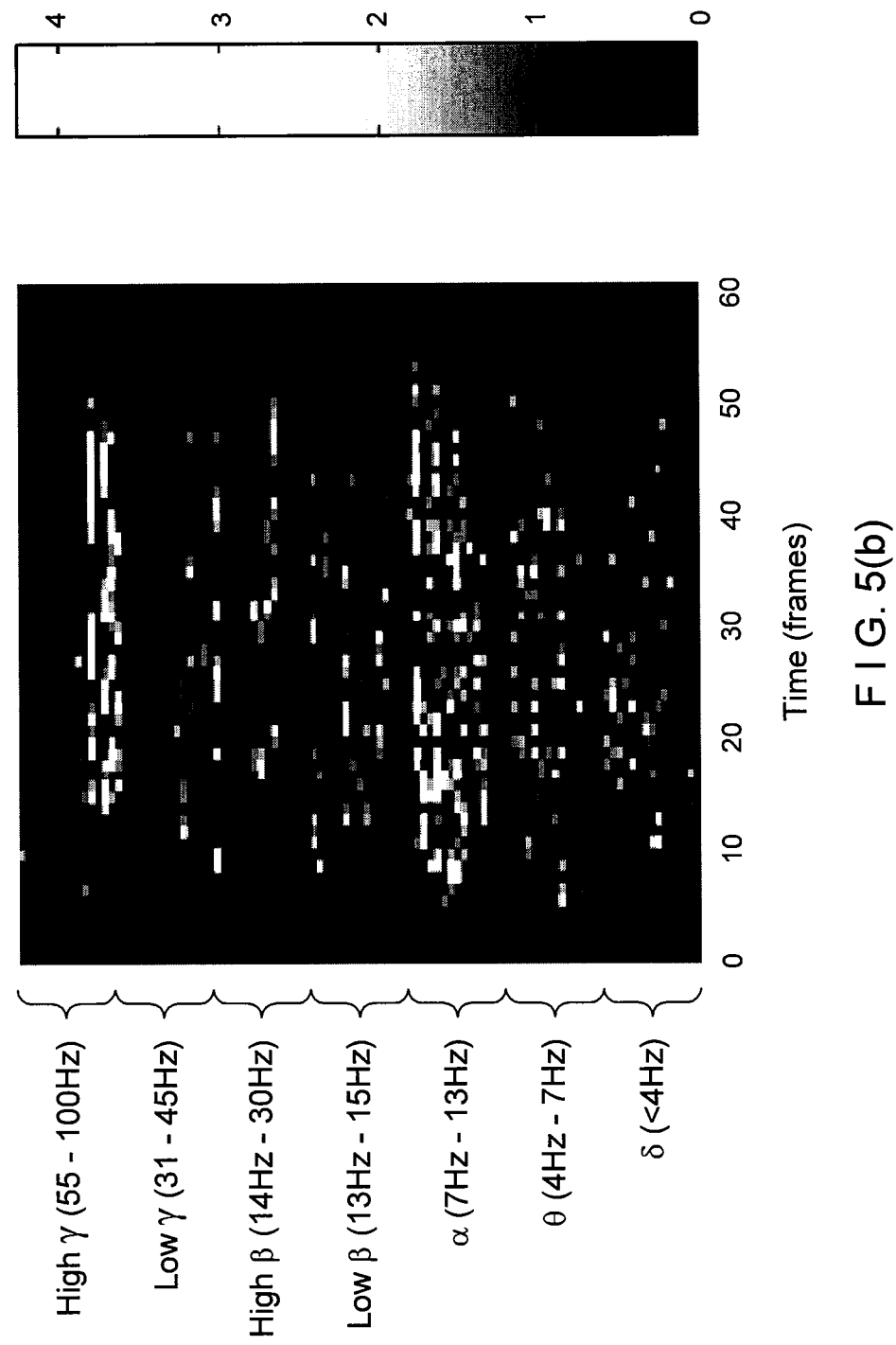
FIG. 5b is an illustration of an exemplary graph that represents an input sensitivity of convolutional networks performed on 5 minute patterns of wavelet coherence.

FIG. 5(*a*) shows a graph of an exemplary sensitivity analysis for patient 12 illustrated in FIG. 4, and FIG. 5(*b*) shows a graph of an exemplary sensitivity analysis for patient 08 of FIG. 4. Indeed, FIGS. 5(*a*) and 5(*b*) illustrate the graphs of an input sensitivity of convolutional networks performed on 5 minute patterns of nonlinear interdependence (see FIG. 5(*a*)) and wavelet coherence (see FIG. 5(*b*)) respectively. Wavelet coherence in FIG. 5(*b*) is the only frequency-specific feature. In FIG. 5(*a*), a classifier appears as being sensitive to interdependence features measured between two extrafocal EEG channels TLB2 and TLB3, whereas a classifier in FIG. 5(*b*) appears as being sensitive mostly to synchronization features in the high gamma range and in the alpha range.

Exemplary Analysis

Exemplary machine learning techniques described herein have been shown to perform at a higher success than previously known seizure prediction methods. For each patient, e.g., a combination of feature type and classifier type that predicted all test seizures without false alarms can be determined. The exemplary results were enabled by a pattern recognition approach applied to spatio-temporal patterns of EEG synchronization features.

Choice of Exemplary Linear or Nonlinear Features

Generally, among bivariate (or multivariate) features, two assumptions about the nature of the model underlying the observed EEG can be made. EEG can either be a realization of a noise-driven linear process, or an observation of a non-linear, possibly chaotic, dynamical system. The exemplary linear or nonlinear hypotheses can imply different sets of mathematical tools and measurements to quantify EEG.

Exemplary linear methods for EEG analysis can assume that over short durations of time, the EEG time series are generated by a system of linear equations with superimposed observation noise. Maximum cross-correlation can be shown to achieve quite a good discrimination performance between interictal and preictal stages. Another assumption about the EEG signal can be its nonlinearity. Although deterministic by nature, exemplary systems of nonlinear differential equations can generate highly complex or even unpredictable ("chaotic") time series. The trajectory or attractor of the generated sequence of numbers can be sensitive to initial conditions: any perturbation in those conditions can grow at an exponential rate along the attractor. Nonlinear, chaotic, dynamical systems can be a plausible model for many complex biological observations, including EEG waveforms. Even if all the variables of a chaotic system are not observed, the original chaotic attractor can be reconstructed due to time-delay embedding of the time series of the limited subset of observed variables, assuming the right embedding dimension and time delay. Similarly, in the state-space, attractors from time-delay embedded observed EEG can be reconstructed.

Comparison with Existing Threshold-Based Seizure Prediction Methods

For example, prior art seizure prediction techniques can resort to a simple binary threshold on a unique EEG feature, and such methods look at "individual pixels" of the EEG-based feature "image" instead of looking at the "full picture", i.e., the relationship between the "pixels" within that "image." Further, the prior art techniques likely fail to capture how features change over time. By contrast, the exemplary embodiment of the system, method and computer-accessible medium according to the present disclosure and as described above can be used to learn to recognize patterns of EEG features.

Exemplary Running-Time Considerations

The exemplary embodiment of the seizure prediction system of the present disclosed as described herein can be ported to human neuro-prosthetics applications. Indeed, the exemplary system can be implemented as, e.g., real-time dedicated software on an embedded computer connected to the patient's intracranial EEG acquisition system.

The exemplary process, which can be a software process implemented on the computing arrangement, from raw numerical EEG to the seizure prediction alarm can be decomposed in 3 exemplary stages, e.g., EEG preprocessing, feature computation and pattern classification. The first exemplary stage (EEG preprocessing) can be implemented by 4 standard Infinite Impulse Response (IIR) filters that have negligible runtime even in real-time signal processing. The third exemplary stage (pattern classification) can be performed, e.g., every minute or every 5 minutes (depending on the pattern size) and can correspond to a few matrix-vector multiplications and simple floating-point numerical operations (addition, multiplication, exponential, logarithm), involving vectors with a few thousand dimensions. The most computationally expensive part is the training (parameter fitting) of the classifier, but it can be done offline and thus does not affect a runtime of the system. The second exemplary stage (feature computation from EEG) can also be relatively fast. For example, it can takes in the order of seconds to process an exemplary 5 minute-long window of 6-channel EEG and extract features such as wavelet analysis-based synchrony (SPLV, Coh or H), nonlinear interdependence S or cross-correlation C. However, since the 5 minute patterns are not overlapping, the exemplary second state can be repeated every minute or 5 minutes (similar to the third exemplary stage).

Exemplary software for computing features from EEG can be implemented in Matlab™, and can be executed, e.g., under its free open-source counterpart, Octave™. Support vector machine classification can be performed using LibSVM™ and its Matlab/Octave interface. Convolutional networks and logistic regression can be implemented in Lush™, an open-source programming environment with extensive machine learning libraries.

Overcoming High Number of EEG Channels Through Exemplary Feature Selection

In addition to real-time capabilities during runtime, the exemplary training phase of the classifier can facilitate further feature selection through sensitivity analysis, namely the discovery of subsets of channels (and if relevant, frequencies of analysis), that have a strong discriminative power for the preictal versus interictal classification task.

Such capability can assist the exemplary system cope with a high number of EEG channels. A number of bivariate features can grow quadratically with the number of channels M, and this quadratic dependence on the number of EEG channels can become problematic when EEG recordings contain many channels (e.g., one or two 64-channel grids with additional strip electrodes). This may slow down both the machine learning (training) and even the runtime (testing) phases. Through sensitivity analysis, a subset of EEG channels which can be used for a seizure prediction performance can be narrowed.

One exemplary approach according to the present disclosure can be long and slow training and evaluation phases using all the EEG channels, followed by an exemplary channel selection with respect to discriminative power, and a second, faster, training phase, with, as an end product, a seizure prediction classifier running on a restricted number of EEG channels. One exemplary advantage of such an approach can be that the channel selection can be done a posteriori with respect to seizure prediction performance. In such exemplary method, the classifier can decide by itself which exemplary subset of channels is the most appropriate.

Exemplary Long, Continuous EEG Recordings

In the EEG Freiburg database, while the exemplary procedure provides, for each patient, with at least 24 hours of interictal and a few hours of preictal, ictal and postictal recordings, it may not cover the whole duration of patient monitoring, and there can be, at times, gaps of several days between the preictal segments and the interictal segments.

Figure 6:
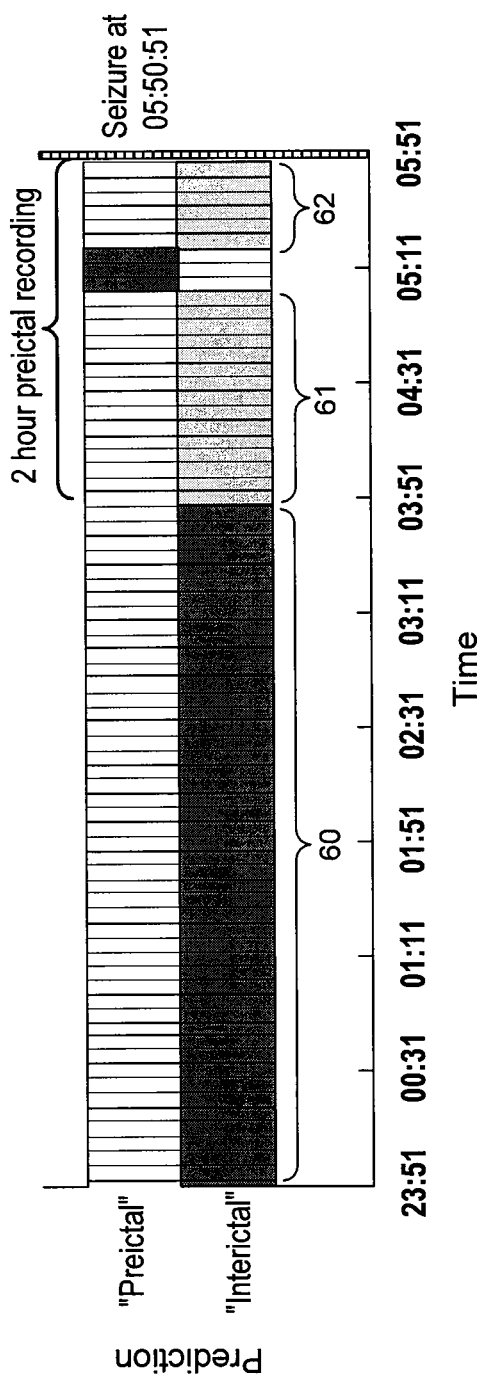
FIG. 6 is an illustration of an exemplary graph of an exemplary performance of a seizure prediction system on a patient on a test dataset comprising a segment of EEG.

FIG. 6 illustrates an exemplary performance of a seizure prediction system on, e.g., patient 8, on a test dataset comprising a segment of EEG going from, e.g., December 8, 11:20 AM through December 9, 5:51 AM. Only the segment after 23:51 PM is shown on the horizontal axis, and a prediction is shown in the vertical axis. The classifier was a convolutional network, and the 5 minute long patterns consisting of wavelet coherence features. Boxes in area 61 illustrate successful predictions for each pattern (true negatives when the pattern is interictal and true positives when the pattern is preictal), and boxes in areas 62 and 63 illustrate false negatives (missed preictal alarms). In this example, there were no false positives/alarms.

As shown in FIG. 6, the exemplary embodiment of method and system according to the present disclosure which can succeed in raising several preictal alarms before the test seizure, without emitting any false alarms. Datasets may contain long, continuous and uninterrupted EEG recordings so that seizure prediction algorithms work at all times.

Exemplary Extension of the Classifier with a Memory of Previous Ictal States

FIGS. 7a and 7b illustrate exemplary graphs of probabilistic state space models with temporal dynamics, that can be used as an architecture and training procedure for RNNs. This exemplary technique can enable learning potentially nonlinear dynamics governing latent variables, and can provide a deterministic inference of hidden states, thereby tailoring them to chaotic time series. For example, an observed (output) Y, control (input) X and latent Z variables can be factorized by observation, control and dynamical models (functions).

An exemplary state space model 700 with temporal dynamics, as shown in FIG. 7(a), can have an observation model 705 that links a time slice of hidden variables Z(t) 730 to co-occurring observed/output variables Y(t) 720, a dynamical model 710 that expresses the dependency of latent variables Z(t) 730 on d previous latent Z(t–1), . . . , Z(t–p) and visible Y(t–1), . . . , Y(t–p) variables. Optionally, a control model 715 relates additional visible variables also called control/input variables X(t) 740 to Z(t) 730 and/or output variables Y(t) 720. Input variables X(t) 740 can also be used without control model 715, as an additional input to either the observation model 705 or the dynamical model 710. This generative state space model 700 can capture dependencies between the visible and latent time series by assigning a scalar energy to each configuration of the hidden and observed variables, as well as to model parameters. State space models 700 can be trained using a deterministic gradient descent-based version of the Expectation-Maximization (EM) algorithm, having iterative inference of the latent variables and learning of the dynamic, observation and control models 710, 705, 715, respectively.

During inference, values of all the model parameters can be clamped and the hidden variables can be relaxed to minimize the energy. During learning, model parameters can be optimized to give lower energy to the current configuration of hidden and observed variables. State space models can be viewed as a gradient descent version of Dynamic Bayesian Networks such as Hidden Markov Models, tailored to deterministic dynamical systems. State space models can overcome the vanishing gradient problem that occurs during the training of an RNN and can compare to other RNN training algorithms.

The exemplary state space model 750 of FIG. 7(b) can be used to predict epileptic seizure prediction from EEG by extending the exemplary model 700 shown in FIG. 7(a). The dependency on the inputs X(t) 780 (patterns of bivariate features) can be modeled by a convolutional network for regression, using the same or similar exemplary architecture as in FIG. 2, e.g., with a multivariate output instead of a classification module. Two types of exemplary state space model architectures can be used: the inputs will either be factored in the dynamical model 755 or in the observation model 765.

As shown in FIG. 7(b), instead of classifying patterns X(t) 780 into Y=1 preictal or Y=0 interictal, the inverse of the time to the next seizure Y (t) 760 is regressed. Low or zero values of Y(t) 760 can represent interictal stages, whereas an increasing value of Y(t) 760 can represent an imminent seizure. The latent variables Z(t) 770 can represent either a low-dimensional embedding of input patterns X(t) 780 through control model 715, with autoregressive time dependencies 755 and with observation model 765 performing the regression of Z(t) 770 onto the time-to-next-seizure Y (t) 760, or a memory variable that is used as an additional input to dynamical model 755. Such exemplary memory variable can be used for a memory-based classifier to reduce the probability of false sporadic alarms. Such exemplary seizure prediction system can enable neuroprosthetic applications such as implantable devices capable of warning the patient of an upcoming seizure or local drug-delivery.

Exemplary Embodiments

Figure 8:
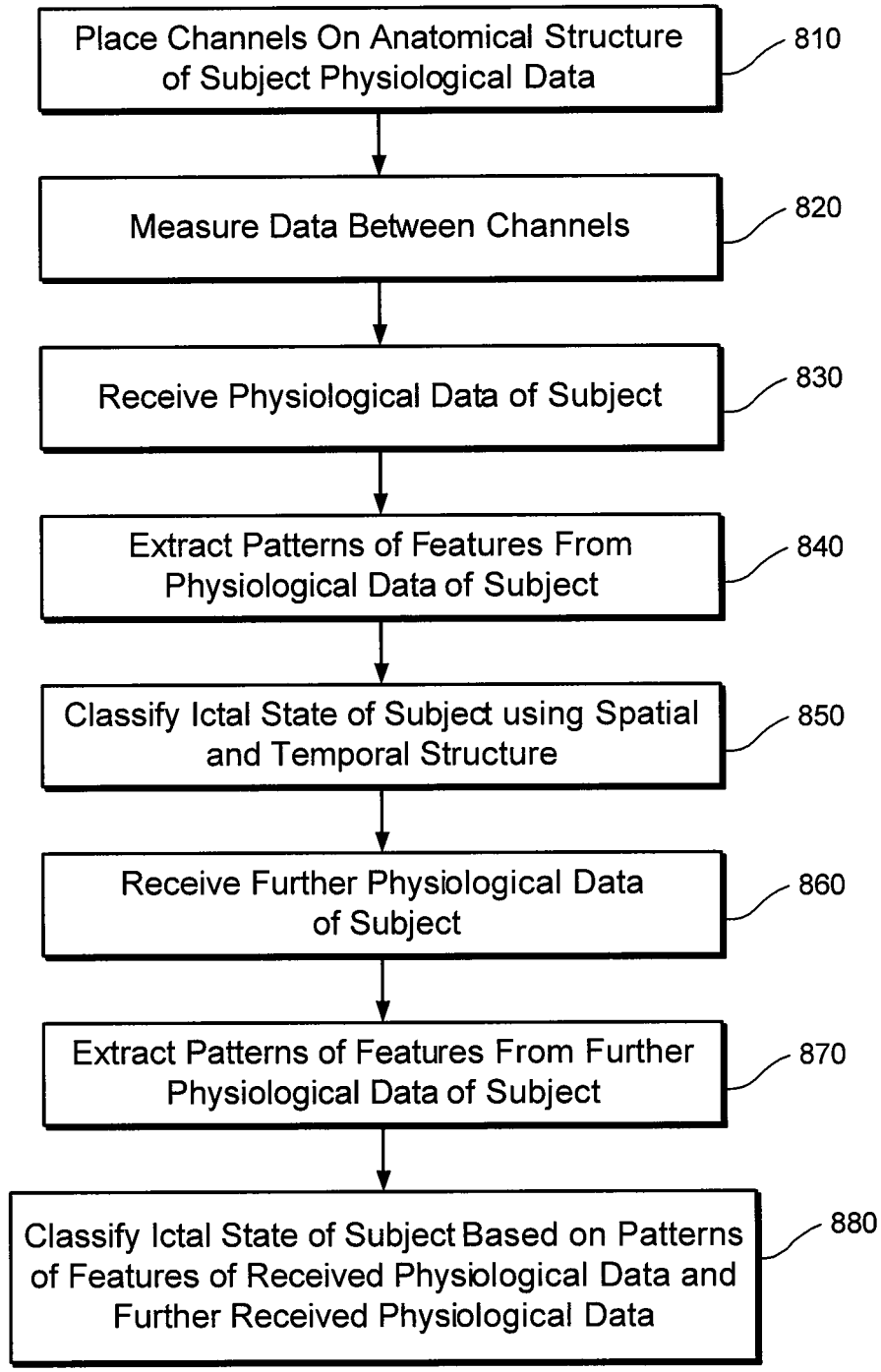
FIG. 8 illustrates a flow diagram according to an exemplary method of the present disclosure.

FIG. 8 illustrates a flow diagram according to an exemplary method for classifying at least one state of a subject according to the present disclosure. Initially, e.g., at step 810, channels can be placed on an anatomical structure, such as a brain, of a subject. Each of the channels can be provided at a different location on an anatomical structure from a location of another one of the channels. The data can be measured between the channels at step 820. Typically, data is measured between two channels. Physiological data is then received of the subject at step 830. The 13. The physiological data can be at least one of EEG data, multichannel EEG data, fMR1 data, MEG data, EKG data, pulse data, respiration data, temperature data, eye movement data or blood chemistry data.

At step 840, one or more patterns of features can be extracted from the physiological data. Each of the features can be a measurement between at least two channels for measuring the physiological data. The one or more patterns of features can be represented by two-dimensional data, such as data of time versus a pair of channels, or time versus a pair of channels and frequency. The one or more patterns of features can also be represented by three-dimensional data, such as data of time versus a pair of channels versus frequency.

The one or more patterns of features can be spatially-varying, time-varying, or frequency-varying. The exemplary features can be bivariate features, which can be based on a measure of a synchronization among one or more subsets of the physiological data, where a measure of the synchronization can be based on at least one of a cross-correlation, a nonlinear interdependence, a difference of Lyapunov exponents or a phase-locking synchrony. The synchrony can be one of a phase-locking statistic, an entropy of a phase difference and distribution, or a coherence. The exemplary features can be unaveraged, or can be consecutive features.

At step 850, an ictal state of the subject can be classified using a spatial structure and a temporal structure of the one or more patterns of features. The ictal state can be classified using a computing arrangement. The computing arrangement according to an exemplary embodiment of the present disclosure can comprise a trained classifier executed by a computer. The exemplary computing arrangement can use convolutional networks to classify the ictal state of the subject. The exemplary temporal structure of the one or more patterns of features can comprise a local time structure.

The exemplary classifying procedure can comprise at least one of an ictal classification, a peri-ictal classification, a pre-ictal classification, and an interictal classification. The ictal state can comprise a seizure, a stroke or a headache. The classifying procedure can discriminate between pre-ictal and inter-ictal states, and can be performed using at least one of a logistic regression or a support vector machine. For example, the classifying procedure can comprise regularizing the at least one state using a lasso regularization or an L1-norm regularization, or regularizing the at least one state using a ridge regularization or an L2-norm regularization.

Such exemplary classifying procedure can comprise training the at least one state using a stochastic gradient descent, and/or by training the at least one state by determining finite impulse response filters of at least a portion of the features.

A sensitivity analysis on the patterns of features can be performed, e.g., before classifying the at least one state. The sensitivity analysis can be used to evaluate an importance of a particular feature according to a spatial location, time or a frequency location in the pattern of features thereof.

The received physiological data can be stored, electronically or manually. At step 860, e.g., further physiological data for the subject can be received at a later time, which can be seconds, minutes, hours or days later. At step 870, one or more further patterns of features can be extracted from the further physiological data of the subject. At step 880, an ictal state of the subject can be classified based on the patterns of features from the received physiological data and the further patterns of features based on the further physiological data, which can be performed by a computing arrangement. Thus, the ictal state of the subject can be classified using a spatial structure and a temporal structure of the one or more patterns of features received earlier, and a spatial structure and a temporal structure of the one or more patterns of features received later. Thus, the ictal state is based on a "memory" of the classifier or computing arrangement.

Figure 9:
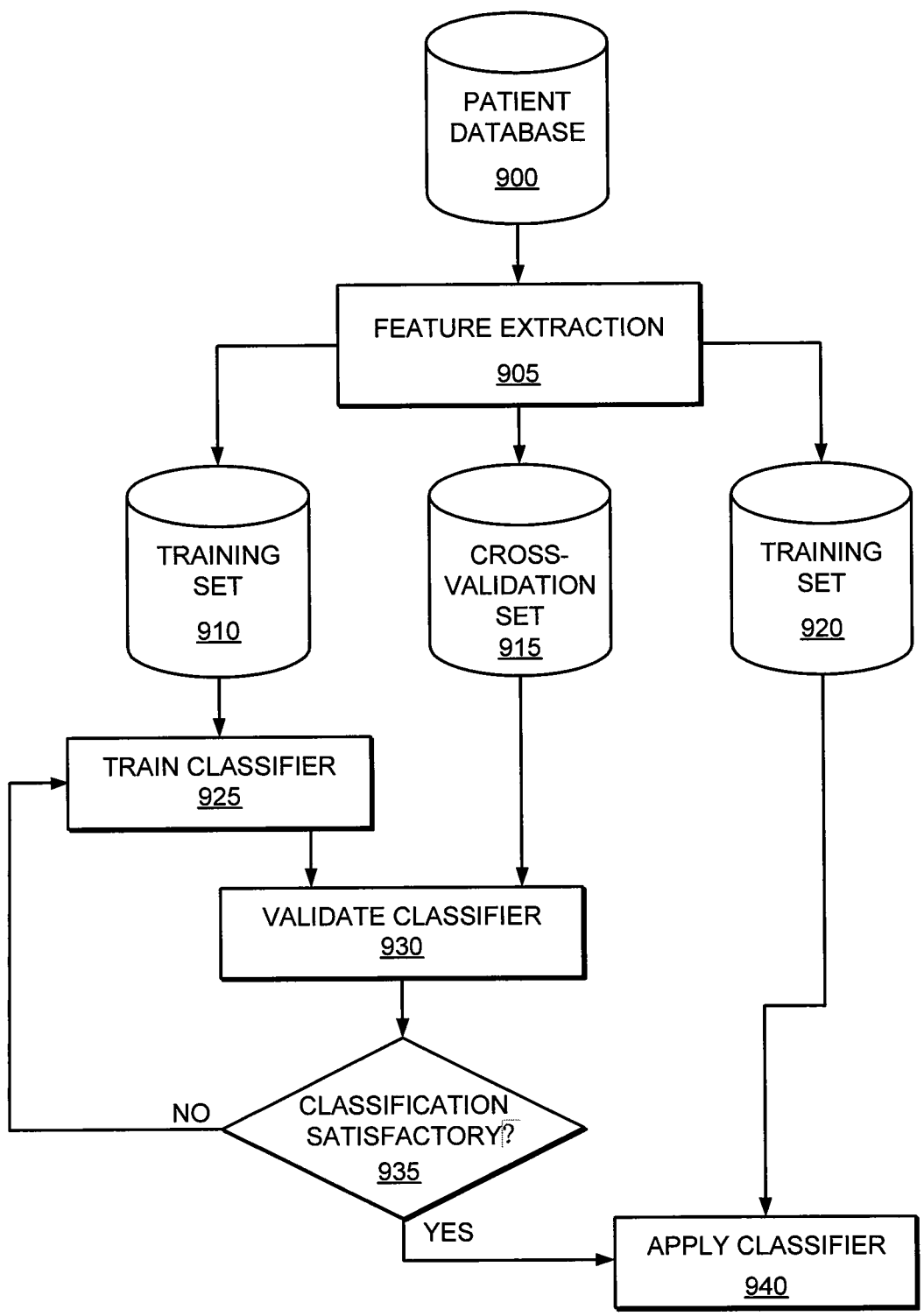
FIG. 9 is a diagram of a combination of an exemplary method and an exemplary system of an ictal state classification that can use exemplary physiological data.

FIG. 9 illustrates a diagram of a combination of an exemplary method and an exemplary system that can provide an ictal state classification using exemplary physiological data. For example, a patient database 900 can store information and physiological data of one or more patients. Physiological data, such as electrophysiological data, specific to a given patient can be used. Exemplary patterns of features can be extracted at 905 from the physiological data in the patient database 900, where such exemplary extraction can include extracting bivariate features, and then organizing the features into exemplary patterns.

These exemplary patterns can be separated into, e.g., 3 exemplary non-overlapping sets: training set 910, cross-validation set 915 and testing set 920. Training set 910 can be directly used to optimize parameters of a classifier. The training set 910 can be used to train a classifier at 925. After each training session, the classifier can be evaluated on cross-validation data at 930. Data from the cross-validation set 915 is validating at 930. If the performance on cross-validation data is satisfactory at 935, then the set of classifier parameters is retained, then the classifier is applied to test data at 940. If the performance on cross-validation data is not satisfactory at 935, then the classifier can be trained at 925. The data from the testing set 920 can be applied to the classifier at 940 directly. Once the classifier is trained and validated, it can be applied in the testing set 920 to test data. Such test data can represent patterns of features computed on electrophysiological data acquired at a later time, in normal operating mode.

Exemplary feature extraction at 905 can comprise a computation and extraction of patterns of bivariate features from exemplary electrophysiological data. First, an electrophysiological signal as recorded on N different channels can be input to a subsystem. Second, exemplary bivariate features can be computed on all $N*(N-1)/2$ pairs (i.e., on all combinations of 2 channels out of N channels). These features can be computed on exactly the same time intervals $\Delta t$ and measure bivariate relationships between any two channels. Third, the features can be computed at consecutive time intervals. Fourth, exemplary features from different time intervals and coming from different pairs of channels can be organized into 2-D arrays of time vs. pairs of channels. Alternatively, these arrays can be organized as 2-D arrays of time vs. pairs of channels and frequencies (in the specific case when the features are frequency-specific). Alternatively, this data can be arranged as 3-D arrays of time vs. pairs of channels vs. frequencies. All such arrangements can be exemplary patterns of features.

The exemplary classifier can be trained as shown in FIG. 9 by various methods. In one exemplary method, first, for a collection of time points t, t+1, t+2, etc., patterns of bivariate features can be extracted (respectively X(t), X(t+1), X(t+2), etc.). The exemplary corresponding labels are associated using clinical data about the patient and the exact times when seizures have occurred. These exemplary labels can either be binary (e.g., 0 if long before a seizure, and 1 if less than 2 hours before a seizure), or they can be continuous and represent the time remaining before the next seizure. These exemplary labels are respectively Y(t), Y(t+1), Y(t+2), etc. The above data can be referred to as training data, such as in training set 910. This data can be used to optimize an exemplary classifier, such as a convolutional network, so that it correctly associates the right label Y(t) to the corresponding pattern of features X(t+1). This training can comprise iterative adjustment of the parameters of the classifier.

Second, regularization constraints can be added to the exemplary optimization process. Third, once the training phase of the classifier is complete, the classifier can be described by its parameters. These exemplary parameters can then be used to classify new, previously unseen, out-of-sample data. Third, a sensitivity analysis can be conducted on the parameters of the classifier to determine which features within the patterns of features contribute the most to the correct classification.

Figure 10:
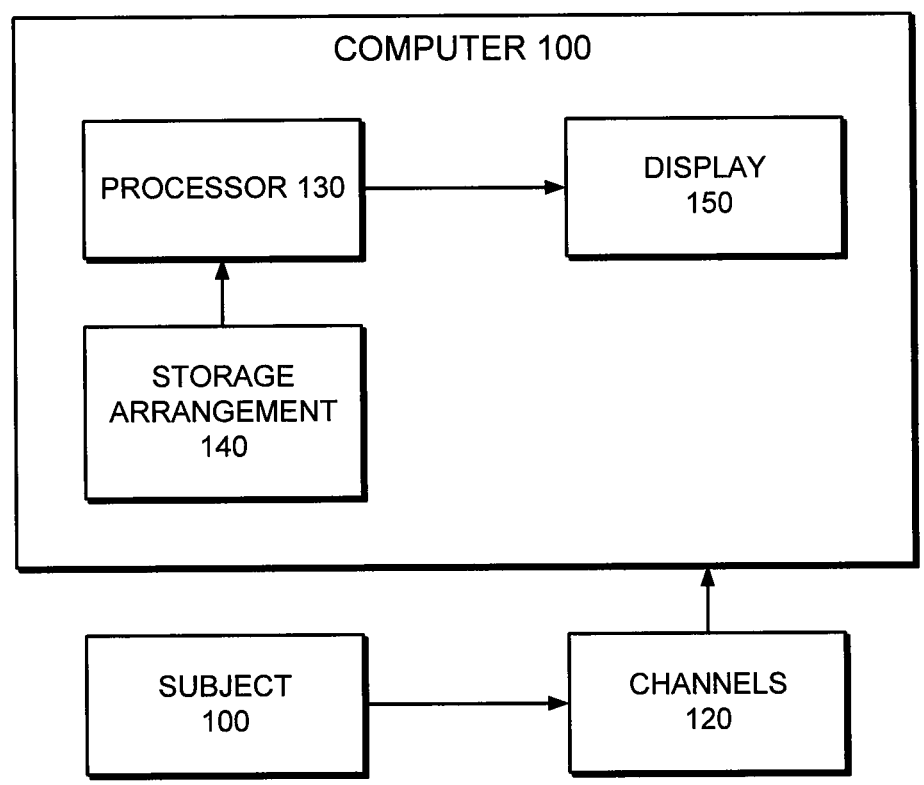
FIG. 10 illustrates a block diagram of an exemplary embodiment of a system according to the present disclosure.

FIG. 10 illustrates a block diagram of an exemplary embodiment of a system according to the present disclosure. For example, a computer 100 can be provided having a processor 130 which can be configured or programmed to perform the exemplary steps and/or procedures of the exemplary embodiments of the techniques described above. For example, a subject 110 can be positioned and an anatomical structure can be selected on the subject 110, and channels 120 can be placed on the anatomical structure, as provided for in step 810 above. Data between the channels can be measured by the computer 100 itself, or by an external device (not shown) such as by an EEG. These measurements can be provided from the device to the computer 100, which can be transmitted to the processor 130 and/or storage arrangement 140.

According to one exemplary embodiment of the present disclosure, the data can be stored in a storage arrangement 140 (e.g., hard drive, memory device, such as RAM, ROM, memory stick, floppy drive, etc.). The processor 130 can access the storage arrangement 140 to execute a computer program or a set of instructions (stored on or in the storage arrangement 630) which perform the procedures according to the exemplary embodiments of the present disclosure. Thus, e.g., when the processor 130 performs such instructions and/or computer program, the processor 130 can be configured or programmed to perform the exemplary embodiments of the procedures according to the present disclosure, as described above herein.

For example, the processor 130 can receive physiological data for the subject, extract one or more patterns of features from the physiological data, and classify the at least one state of the subject using a spatial structure and a temporal structure of the one or more patterns of features, wherein at least one of the at least one state is an ictal state. The physiological data can be received directly from the subject 110 or accessed from the storage arrangement 140.

A display 150 can also be provided for the exemplary system of FIG. 10. The storage arrangement 140 and the display 150 can be provided within the computer 100 or external from the computer 100. The information received by the processor 130 and the information determined by the processor 130, as well as the information stored on the storage arrangement 140 can be displayed on the display 150 in a user-readable format.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements, and methods which, although not explicitly shown or described herein, embody the principles of the invention and are thus within the spirit and scope of the invention. In addition, all publications and references referred to above are incorporated herein by reference in their entireties. It should be understood that the exemplary procedures described herein can be stored on any computer accessible medium, including a hard drive, RAM, ROM, removable discs, CD-ROM, memory sticks, etc., and executed by a processing arrangement which can be a microprocessor, mini, macro, mainframe, etc.

What is claimed is:

1. A method for classifying at least one state of a subject, comprising:
    receiving physiological data for the subject, the physiological data including a plurality of features having at least a first feature and a second feature that are based on a respective measure of a synchronization for at least one pair of channels, wherein the synchronization associated with (i) the first feature is over a first time period; and (ii) the second feature is over a second time period;
    generating an array of the features having the first and second features as entries in the array;
    generating a multilayer convolutional neural network, wherein a first layer and a second layer of the multilayer convolutional neural network is based on a convolution across time, and a third layer of the multilayer convolutional neural network is based on a convolution across time, space and frequency; and
    using a computer hardware arrangement, classifying the at least one state based on information provided in the array using the at least one multilayer convolutional neural network.

2. The method of claim 1, wherein the features are spatially-varying and time-varying.

3. The method of claim 1, wherein a temporal structure of the features comprises a local time structure.

4. The method of claim 1, wherein the features comprise bivariate features.

5. The method of claim 1, wherein the classifying procedure is performed using at least one of a logistic regression or a support vector machine.

6. The method of claim 1, further comprising:
    electronically storing the received physiological data;
    receiving further physiological data for the subject; and
    using the computing arrangement, classifying the at least one state of the subject based on the further physiological data.

7. The method of claim 4, wherein the bivariate features are based on the measure of the synchronization which is based on wavelet analysis-based synchrony values grouped in one or more frequency bands.

8. The method of claim 1, wherein the first feature is based on a first frequency and the second feature is based on at least one second frequency.

9. The method of claim 1, wherein at least one further layer of the multilayer convolutional neural network is based on subsampling.

10. The method of claim 1, wherein the channels are EEG channels.

11. The method of claim 1, wherein the plurality of features includes a third feature and a fourth feature that are based on a respective measure of the synchronization for at least one second pair of channels, wherein the synchronization associated with (i) the third feature is over the first time period; and (ii) the fourth feature is over the second time period.

12. The method of claim 1, wherein the plurality of features includes a third feature and a fourth feature that are based on a respective measure of the synchronization for at least one second pair of channels, wherein the synchronization associated with (i) the third feature is over the first time period; and (ii) the fourth feature is over the second time period.

13. A non-transitory computer-accessible medium for classifying at least one state of a subject, the computer-accessible medium including instructions thereon, wherein, when a computing arrangement executes the instructions, the computing arrangement is configured to perform procedures comprising:
  receiving physiological data for the, the physiological data including a plurality of features having at least a first feature and a second feature that are based on a respective measure of a synchronization for at least one pair of channels, wherein the synchronization associated with (i) the first feature is over a first time period; and (ii) the second feature is over a second time period;
  generating an array of the features having the first and second features as entries in the array;
  generating a multilayer convolutional neural network, wherein a first layer and a second layer of the multilayer convolutional neural network is based on a convolution across time, and a third layer of the multilayer convolutional neural network is based on a convolution across time, space and frequency; and
  classifying the at least one state based on the array using the at least one multilayer convolutional neural network.

14. The computer-accessible medium of claim 13, wherein the features are represented by two-dimensional data.

15. The computer-accessible medium of claim 13, wherein the features are represented by three-dimensional data.

16. The computer-accessible medium of claim 13, wherein the at least one state comprises at least one of an ictal classification, a peri-ictal classification, a pre-ictal classification or an interictal classification.

17. The computer-accessible medium of claim 13, wherein the features comprise bivariate features.

18. The computer-accessible medium of claim 13, wherein the computer arrangement is further configured to maintain a memory of previously received physiological data after classifying the ictal state.

19. The computer-accessible medium of claim 13, wherein the first feature is based on a first frequency, and the second further feature is based on at least one second frequency.

20. The computer-accessible medium of claim 13, wherein at least one further layer of the multilayer convolutional neural network is based on subsampling.

21. The computer-accessible medium of claim 13, wherein the channels are EEG channels.

22. The computer-accessible medium of claim 13, wherein the computing arrangement is further configured to generate (i) a fourth layer of the multilayer convolutional neural network is generated based on subsampling, and (ii) a fifth layer of the multilayer convolutional neural network based on the convolution across time.

23. A system for classifying at least one state of a subject, which comprises:
  a computer hardware arrangement configured to:
    receive physiological data for the, the physiological data including a plurality of features having at least a first feature and a second feature that are based on a respective measure of a synchronization for at least one pair of channels, wherein the synchronization associated with (i) the first feature is over a first time period; and (ii) the second feature is over a second time period;
    generate an array of the features having the first and second features as entries in the array;
    generate a multilayer convolutional neural network, wherein a first layer and a second layer of the multilayer convolutional neural network is based on a convolution across time, and a third layer of the multilayer convolutional neural network is based on a convolution across time, space and frequency; and
    classify the at least one state based on the array using a trained classifier module that uses the at least one multilayer convolutional neural network.

24. The system of claim 23, wherein the features are represented by three-dimensional data.

25. The system of claim 24, wherein the three-dimensional data is data of time versus a particular pair of channels versus frequency.

26. The system of claim 23, wherein the at least one state comprises at least one of an ictal classification, a peri-ictal classification, a pre-ictal classification or an interictal classification.

27. The system of claim 23, wherein the physiological data is at least one of EEG data, multi-channel EEG data, fMRI data, MEG data, EKG data, pulse data, respiration data, temperature data, eye movement data or blood chemistry data.

28. The system of claim 27, wherein the features are spatially-varying and time-varying.

29. The system of claim 28, wherein the features are frequency-varying.

30. The system of claim 23, wherein the classification procedure discriminates between pre-ictal and inter-ictal states.

31. The system of claim 23, wherein a temporal structure of the features comprises a local time structure.

32. The system of claim 23, wherein the features comprise bivariate features.

33. The system of claim 32, wherein the bivariate features are based on the measure of the synchronization for each of the pairs of channels.

34. The system of claim 33, wherein the measure of the synchronization is based on at least one of a cross-correlation, a nonlinear interdependence, a difference of Lyapunov exponents or a phase-locking synchrony.

35. The system of claim 34, wherein the synchrony comprises one of a phase-locking statistic, an entropy of a phase difference and distribution, or a coherence.

36. The system of claim 23, wherein the classification procedure uses at least one of a logistic regression or a support vector machine.

37. The system of claim 23, wherein the classification procedure is causes a regularization of the array using a lasso regularization or an L1-norm regularization.

38. The system of claim 23, wherein the classification procedure is causes a regularization of the array using a ridge regularization or an L2-norm regularization.

39. The system of claim 23, wherein the classification procedure is trained using a stochastic gradient descent.

40. The system of claim 23, wherein the classification procedure is trained by determining finite impulse response filters of at least a portion of the features.

41. The system of claim 40, wherein the features are consecutive features.

42. The system of claim 23, wherein the computer hardware arrangement is further configured to perform a sensitivity analysis on the features before classifying the at least one state.

43. The system of claim 42, wherein the sensitivity analysis is used to evaluate an importance of a particular feature according to a spatial location, time or a frequency location in the features thereof.

44. The system of claim 38, wherein the classification procedure uses a support vector machine and the features that are in a training dataset and that serve as support vectors for the classification procedure are used to evaluate an electrophysiological recording or the development of ictal states over time.

45. The system of claim 33, wherein the measure of the synchronization is based on wavelet analysis-based synchrony values grouped in one or more frequency bands.

46. The system of claim 23, wherein the first feature is based on a first frequency, and the second feature is based on at least one further frequency.

47. The system of claim 23, wherein at least one further layer of the multilayer convolutional neural network is based on subsampling.

48. The system of claim 23, wherein the channels are EEG channels.

49. The system of claim 23, wherein the plurality of features includes a third feature and a fourth feature that are based on a respective measure of the synchronization for at least one second pair of channels, wherein the synchronization associated with (i) the third feature is over the first time period; and (ii) the fourth feature is over the second time period.

* * * * *